US009592259B2

(12) United States Patent
Dresch et al.

(10) Patent No.: US 9,592,259 B2
(45) Date of Patent: Mar. 14, 2017

(54) APC-MEDIATED TOLERANCE INDUCTION FOR THERAPY OF MULTIPLE SCLEROSIS

(71) Applicant: Universität Zürich Prorektorat MNW, Zürich (CH)

(72) Inventors: Christiane Dresch, Seattle, WA (US); Bruna de Andrade Pereira, Zürich (CH); Mathias Ackermann, Basserdorf (CH); Cornel Fraefel, Trüllikon (CH)

(73) Assignee: University of Zurich, Zürich (CH)

( * ) Notice: Subject to any disclaimer, the term of this patent is extended or adjusted under 35 U.S.C. 154(b) by 0 days.

(21) Appl. No.: 14/347,439

(22) PCT Filed: Sep. 26, 2012

(86) PCT No.: PCT/EP2012/068954
§ 371 (c)(1),
(2) Date: Mar. 26, 2014

(87) PCT Pub. No.: WO2013/045488
PCT Pub. Date: Apr. 4, 2013

(65) Prior Publication Data
US 2014/0242037 A1    Aug. 28, 2014

Related U.S. Application Data

(60) Provisional application No. 61/573,200, filed on Sep. 26, 2011.

(30) Foreign Application Priority Data

Sep. 26, 2011  (EP) .................................... 11182700

(51) Int. Cl.
| A61K 38/17 | (2006.01) |
| A61K 48/00 | (2006.01) |
| A61K 35/76 | (2015.01) |
| A61K 31/10 | (2006.01) |
| A61K 35/12 | (2015.01) |
| C12N 15/11 | (2006.01) |
| A61K 31/711 | (2006.01) |
| A61K 38/16 | (2006.01) |
| C07K 14/47 | (2006.01) |

(52) U.S. Cl.
CPC .............. *A61K 35/76* (2013.01); *A61K 31/10* (2013.01); *A61K 35/12* (2013.01); *A61K 48/0058* (2013.01); *C12N 15/11* (2013.01); *C12N 2830/008* (2013.01)

(58) Field of Classification Search
None
See application file for complete search history.

(56) References Cited

U.S. PATENT DOCUMENTS

| 7,090,982 B2 * | 8/2006 | Warren ............. C07K 14/4713 435/6.16 |
| 2003/0049797 A1 * | 3/2003 | Yuki ..................... C07K 14/28 435/69.7 |
| 2008/0103091 A1 * | 5/2008 | Siahaan ........... C07K 14/70503 424/1.69 |
| 2008/0247984 A1 | 10/2008 | Messersmith et al. |

FOREIGN PATENT DOCUMENTS

| WO | WO-2011028031 A2 | 3/2011 |
| WO | WO-2011084710 A1 | 7/2011 |

OTHER PUBLICATIONS

Hartgers et al., "Genomic organization, chromosomal localization, and 5' upstream region of the human DC-STAMP gene" 53 Immunogenetics 145-149 (2001).*
Wingerchuk et al., "Multiple Sclerosis: Current and Emerging Disease-Modifying Therapies and Treatment Strategies" 89(2) Mayo Clinic Proceedings 224-240 (2014).*
Martin et al., "Immunlogical Aspects of Demyelinating Diseases" 10 Annual Review of Immunology 153-187 (1992).*
Gerwitz et al. "Nucleic Acid Therapeutics: State of the Art and Future Prospects" 92(3) Blood 712-736 (1998).*
Cameron "Recent Advances in Transgenic Technology" 7 Molecular Bioltechnology 253-265 (1997).*
Eixarch et al., "Tolerance Induction in Experimental Autoimmune Encephalomyelitis Using Non-myeloablative Hematopoietic Gene Therapy With Autoantigen" 17(5) Molecular Therapy 897-905 (2009).*
Hartgers, F.C. et al. 2000 "DC-STAMP, a novel multimembrane-spanning molecule preferentially expressed by dendritic cells". Eur. J. Immunol. 2000. 30: 3585-3590.
Hosseini, H., et al 2011 "Non-myeloablative transplantation of bone marrow expressing self-antigen establishes peripheral tolerance and completely prevents autoimmunity in mice" Gene Therapy, 1-10.
Kawamura, K., et al. 2008 "Myelin-reactive type B T cells and T cells specific for low-affinity MHC-binding myelin peptides escape tolerance in HLA-DR transgenic mice". J Immunol. Sep. 1, 2008:181(5):3202-11.
Andrade Pereira, B. de, et al. 2012 "Transcriptional targeting of DCs with lentiviral vectors induces antigen-specific tolerance in a mouse model of multiple sclerosis", Gene Therapy. 20, 556-566.
Chan, J., et al. 2008 "Transplantation of bone marrow transduced to express self-antigen establishes deletional tolerance and permanently remits autoimmune disease". J Immunol. 181(11):7571-80.
Hansen B.E, et al. 2011 "The HLA-DP2 protein binds the immunodominant epitope from myelin basic protein, MBP85-99, with high affinity". Tissue Antigens. 77(3):229-34.

(Continued)

Primary Examiner — Nancy J Leith
(74) Attorney, Agent, or Firm — Dinsmore & Shohl L.L.P.; Weston R. Gould

(57) ABSTRACT

The invention relates to transgene expression constructs—particularly self inactivating lentiviral vectors—comprising a dendritic cell specific promoter controlling the expression of autoantigen proteins, namely myelin basic protein, proteolipid protein and myelin oligodendrocyte glycoprotein, for use in the therapy of multiple sclerosis.

11 Claims, 9 Drawing Sheets

(56) References Cited

OTHER PUBLICATIONS

Lois, C., et al. 2002 "Germline transmission and tissue-specific expression of transgenes delivered by lentiviral vectors". Science. 295(5556):868-72. Epub Jan. 10, 2002.

Dresch, C. et al. 2008 "Lentiviral-Mediated Transcriptional Targeting of Dendritic Cells for Induction of T Cell Tolerance in Vivo", The Journal of Immunology. 181, 4495-4506.

Martin, R., et al. 1990 "Fine specificity and HLA restriction of myelin basic protein-specific cytotoxic T cell lines from multiple sclerosis patients and healthy individuals". J Immunol. 145(2):540-8.

Mendel, I., et al. 1995 "A myelin oligodendrocyte glycoprotein peptide induces typical chronic experimental autoimmune encephalomyelitis in H-2b mice: fine specificity and T cell receptor V beta expression of encephalitogenic T cells". Eur J Immunol. 25(7):1951-9.

Miyoshi, H., et al. 1998 "Development of a self-inactivating lentivirus vector". J Virol. 72(10):8150-7.

Pelfrey, C.M. et al., "Identification of a novel T cell epitope of human proteolipid protein (residues 40-60) recognized by proliferative and cytolytic CD4+ T cells from multiple sclerosis patients," J Neuroimmunol. 46(1-2):33-42 (1993).

Mangalam, A.K., et al., "Identification of T cell epitopes on human proteolipid protein and induction of experimental autoimmune encephalomyelitis in HLA class II-transgenic mice," Eur J Immunol. 34(1): 280-90 (2004).

Forsthuber, T.G. et al., "T cell epitopes of human myelin oligodendrocyte glycoprotein identified in HLA-DR4 (DRB1*0401) transgenic mice are encephalitogenic and are presented by human B cells," J Immunol., 167(12):7119-25 (2001).

Ko, H. et al., "Targeting MOG expression to dendritic cells delays onset of experimental autoimmune disease," Autoimmunity, 44, 177-187 (2011).

Brubaker, C.E. et al., "Enzymatically Degradable Mussel-Inspired Adhesives Hydrogel", Biomacromolecules, 2011, 12, 4326-4334.

Gurnani, V. et al., "Cellulose based macromolecular chelator having pyrocatechol as an anchored ligand: synthesis and applications as metal extractant prior to their determination by flame atomic absorption spectrometry," Talanta, 61, 2003, 889-903.

Krogsgaard, M. et al., "Self-healing mussel-inspired multi-pH-responsive hydrogels," Biomacromolecules, 2013, 14, 297-301.

Lee, B.P. et al., "Synthesis and Gelation of DOPA-Modified Poly-(ethylene glycol) Hydrogels," Biomacromolecules, 2002, 3, 1038-1047.

Ryu, J.H. et al., "Catechol-functionalized chitosan/pluronic hydrogels for tissue adhesives and hemostatic materials," Biomacromolecules, 2011, 12, 2653-2659.

Yu, M and Deming, T.J., "Synthetic polypeptide mimics of marine adhesives," Macromolecules, 1998, 31, 4739-4745.

"Gene Therapy for Diseases", ASGCT—American Society of Gene & Cell Therapy, downloaded from http://www.asgct.org/about_gene_therapy/diseases.php, Oct. 13, 2015, one page.

Dellovade, T. et al., "ATX-MS, An Immunotolerizing Agent, Halts Disease Progression and Reduces CNS Inflammation in Rodent Models of Multiple Sclerosis (P1.216)", Neurology Apr. 8, 2014 vol. 82 No. 10 Supplement P1-216, one page.

Kaushansky et al., PLoS One, vol. 6, 2011, e27860, pp. 1-13.

Zhong et al., The Journal of Clinical Investigation, 2002, vol. 110, pp. 81-90.

\* cited by examiner

A

B

A

B

A

APC-MEDIATED TOLERANCE INDUCTION FOR THERAPY OF MULTIPLE SCLEROSIS

BACKGROUND

The cause of multiple sclerosis (MS or encephalomyelitis disseminata) is unknown and the pathogenic processes leading to disease development are incompletely understood. Current knowledge supports a T cell mediated autoimmune pathogenesis targeting myelin components or myelin-producing cells. MS and its animal model, experimental autoimmune encephalomyelitis (EAE), are characterized by the activation and accumulation of antigen presenting cells (APCs) and auto-reactive lymphocytes within the central nervous system (CNS). Some of the myelin proteins known to be recognized by self-reactive T cells include myelin basic protein (MBP), proteolipid protein (PLP) and myelin oligodendrocyte glycoprotein (MOG).

Myelin basic protein (MBP) is a major constituent of the myelin sheath of oligodendrocytes and Schwann cells. The genetic data of its human orthologue are published under gene ID 4155 at the US National Centre for Biotechnology Information (NCBI); the human MBP protein data can be accessed at UniProt under P02686.

Proteolipid protein (PLP; lipophilin) is the major myelin protein from the central nervous system. It plays an important role in the formation or maintenance of the multilamellar structure of myelin. The genetic data of its human orthologue are published under NCBI gene ID 5354; the human MBP protein data can be accessed at UniProt under P60201.

Myelin oligodendrocyte glycoprotein (MOG) is a glycoprotein believed to play a role in providing structural integrity to the myelin sheath. The genetic data of its human orthologue are published under NCBI gene ID 4340; the human MBP protein data can be accessed at UniProt under Q16653.

The etiology of multiple sclerosis is not yet completely understood and there is no curative treatment available at present. Autologous, T cell depleted bone marrow transplantation has been shown to be effective and beneficial in clinical trials on multiple sclerosis patients. However, disease relapse due to re-emergence of auto-reactive T cells suggests that specific treatment should consider the induction of permanent immune tolerance. Dynamic changes in the anti-myelin T-cell reactivity pattern (antigen spreading) that have been demonstrated in several studies, however, as well as the difficulty in safely inducing tolerance via altered peptide ligand-based treatment, have raised questions about the usefulness of the current strategies for antigen-specific immunotherapy of multiple sclerosis.

The standard treatment of autoimmune diseases relies on generalized immune-suppression. However, even with the difficulties described above, it is important to design novel antigen-specific forms of therapy, which conserve the ability of the immune system to combat pathogens and cancer. For example, previous studies have shown that bone marrow derived HSC transduced with standard gamma retrovirus vectors expressing MOG or PLP can protect mice from EAE. These investigators used constitutive promoters that can mediate MOG expression in different hematopoietic cells, which may cause adverse side effects. To overcome this limitation, Ko et al. have used the cd11c promoter in the context of standard gamma retrovirus vectors to direct MOG expression to dendritic cells (DCs). Although this strategy delayed disease onset, it did not prevent EAE development (Ko et al., 2010, Eur. J. Immunol. 40, 3499-3509).

Dresch et al. (J. Immunology 2008, 181; 4495-4506) demonstrated that transduction of hematopoietic stem cells (HSC) with self-inactivating (SIN) lentivirus vectors that express EGFP or ovalbumin (OVA) from the DC-specific DC-STAMP promoter results in the transcriptional targeting of transgene expression to DCs and in the antigen specific induction of immune tolerance.

The objective of the present invention is to provide means and methods to allow induction of tolerance to autoantigen reactive immune processes in MS, thus reversing the established autoimmune process, alleviating the symptoms and halting the progress of multiple sclerosis.

SUMMARY

According to a first aspect of the invention, a nucleic acid sequence is provided. This nucleic acid sequence comprises an expressed sequence, which encodes a polypeptide comprising a contiguous sequence of at least nine amino acids contained in a human protein selected from the group of myelin basic protein, proteolipid protein and myelin oligodendrocyte glycoprotein. Said expressed sequence is under transcriptional control of a DC-STAMP promoter sequence.

According to a second aspect of the invention, a lentivirus is provided that comprises a nucleic acid sequence, said nucleic acid sequence comprising an expressed sequence, which encodes a polypeptide comprising a contiguous sequence of at least nine amino acids contained in a human protein selected from the group of myelin basic protein, proteolipid protein and myelin oligodendrocyte glycoprotein under transcriptional control of a DC-STAMP promoter sequence.

According to a third aspect of the invention, an isolated dendritic cell is provided that comprises an expressed nucleic acid sequence encoding a polypeptide comprising a contiguous sequence of at least nine amino acids contained in a human protein selected from the group of myelin basic protein, proteolipid protein and myelin oligodendrocyte glycoprotein under transcriptional control of a DC-STAMP promoter sequence.

According to a fourth aspect of the invention, a pharmaceutical composition for treatment of a demyelinating disease—particularly multiple sclerosis—is provided. Said pharmaceutical composition comprises an isolated dendritic cell comprising an expressed nucleic acid sequence encoding a polypeptide comprising a contiguous sequence of at least nine amino acids contained in a human protein selected from the group of myelin basic protein proteolipid protein and myelin oligodendrocyte glycoprotein under transcriptional control of a DC-STAMP promoter sequence.

According to yet another aspect of the invention, a method of treating multiple sclerosis is provided, comprising providing an isolated dendritic cell according to the invention, to a patient in need thereof.

Moreover, the invention concerns a method of producing a cell preparation for treating multiple sclerosis in a patient, comprising the step of: introducing into a preparation of antigen presenting cells (APC) derived from said patient an expressed nucleic acid sequence according to the invention.

"Preparation of APC" as used herein may refer to any preparation enriched in APC. Such preparations are well-known in the art, and methods of producing them are considered routine. An exemplary, non-limiting type of preparation is a preparation of bone marrow derived hematopoietic stem cells (BM-HSC). Methods of preparing BM-HSC preparations are well-known and routine, and are exemplified inter alia herein.

DETAILED DESCRIPTION

The present invention is based on the surprising finding that expression of an autoantigen encoding transgene in dendritic cells, driven by a promoter sequence specific for dendritic cells, may not only prevent onset of an autoimmune disease, but is able to revert an established autoimmune process and halt progression of a demyelinating disease.

The present invention demonstrates that permanent, antigen-specific tolerance is induced by ex vivo modification of hematopoietic stem cells (HSC) with a vector that expresses antigens involved in MS from a dendritic cell-specific promoter.

According to the invention, an expressed nucleic acid sequence is provided encoding a human autoantigen under transcriptional control of a dendritic cell specific promoter.

A DC-specific promoter sequence in the context of the present invention is a nucleic acid sequence that constitutively expresses the coding sequence under its control in a human immature dendritic cell. A preferred DC-specific promoter sequence is the DC-STAMP promoter sequence, or the 5' untranslated region of the DC-STAMP gene (see Hartgers et al., Eur. J. Immunol. 2000; 30, 3585-90). A particularly preferred DC-specific promoter sequence is the sequence of SEQ ID 02. An alternate preferred DC-specific promoter sequence is the sequence of SEQ ID 19 (GenBank Accession No. AF305068). Still other DC-STAMP promoter regions of interest can be readily amplified by PCR from total genomic DNA using suitable primers as described in Dresch et al (ibid).

According to one embodiment, the expressed sequence encodes a human autoantigen selected from the group of myelin basic protein, proteolipid protein and myelin oligodendrocyte glycoprotein, or a part thereof, under transcriptional control of a DC-specific promoter sequence.

According to one embodiment, the expressed sequence encodes myelin basic protein isoform 1 (SEQ ID 05 and 20) or a fragment thereof. According to another embodiment, the expressed sequence encodes myelin basic protein isoform 2 (SEQ ID 35), isoform 3 (SEQ ID 36), isoform 4 (SEQ ID 06), isoform 5 (SEQ ID 37), isoform 6 (SEQ ID 38) or isoform 7 (SEQ ID 39) or a fragment thereof. According to another embodiment, the expressed sequence encodes myelin proteolipid protein isoform 1 (SEQ ID 07) or a fragment thereof. According to another embodiment, the expressed sequence encodes myelin proteolipid protein isoform DM-20 (SEQ ID 08) or a fragment thereof. According to another embodiment, the expressed sequence encodes myelin oligodendrocyte glycoprotein isoform 1 (SEQ ID 09), isoform 2 (SEQ ID 10), isoform 3 (SEQ ID 11), isoform 4 (SEQ ID 12), isoform 5 (SEQ ID 13), isoform 6 (SEQ ID 14), isoform 7 (SEQ ID 15), isoform 8 (SEQ ID 16), isoform 9 (SEQ ID 17) or isoform 10 (SEQ ID 18); or a fragment thereof.

According to one embodiment, the expressed nucleic acid sequence encodes only a polypeptide part of a human autoantigen. In one embodiment, said polypeptide part represents a common HLA I epitope of said autoantigen. In another embodiment, said polypeptide part represents the major HLA I epitope of said autoantigen. In one embodiment, said polypeptide part represents a common HLA II epitope of said autoantigen. In another embodiment, said polypeptide part represents the major HLA II epitope of said autoantigen. Methods for predicting epitopes are known in the art and are described inter alia in the book "MHC Ligands and Peptide Motifs" by H. G. Rammensee, J. Bachmann and S. Stevanovic.

Exemplary, non-limiting MBP HLA I epitopes that can be useful in the present invention include: MBP84-102, more specifically MBP85-99 (ENPVVHFFKNIVTPR; SEQ ID 21) (Hansen B E et al. Tissue Antigens. 2011 March; 77(3):229-34); MBP154-172 (Martin R et al, J Immunol. 1990 Jul. 15; 145(2):540-8); hMBP64-78 (ARTAHYGSLPQKSHG; SEQ ID 22), hMBP82-100 (DENPVVHFFKNIVTPRTPP; SEQ ID 23), hMBP111-129 (LSRFSWGAEGQRPGFGYGG; SEQ ID 24), and hMBP138-151 (HKGFKGVDAQGTLS; SEQ ID 25) (Kawamura K et al, J Immunol. 2008 Sep. 1; 181(5):3202-11). In some embodiments, a polynucleotide sequence used in the present invention expresses a contiguous sequence of at least nine amino acids contained in one of the above MBP HLA I epitopes. In other embodiments, a polynucleotide sequence used in the present invention expresses one or more of the above MBP HLA I epitopes.

Exemplary, non-limiting PLP HLA I epitopes that can be useful in the present invention include: human PLP 31-70 (CGCGHEALTGTEKLIETYFSKNYQDYEYLINVIHAFQYVI; SEQ ID 26) (Mangalam A K et al, Eur J Immunol. 2004 January; 34(1):280-90), more specifically 40-60 (GTEKLIETYFSKNYQDYEYLI; SEQ ID 27) (Pelfrey C M et al, J Neuroimmunol. 1993 July; 46(1-2):33-42); 91-120 (YTTGAVRQIFGDYKTTICGKGLSATVTGGQ; SEQ ID 28) and 178-228 (NTWTTCQSIAFPSKTSASIGSLCADARMYGVLPWNAFPGKVCGSNLLSICK; SEQ ID 29). In some embodiments, a polynucleotide sequence used in the present invention expresses a contiguous sequence of at least nine amino acids contained in one of the above PLP HLA I epitopes. In other embodiments, a polynucleotide sequence used in the present invention expresses one or more of the above PLP HLA I epitopes.

Exemplary, non-limiting MOG epitopes that can be useful in the present invention include: the mouse MOG epitopes 1-21, 35-55, 67-87, 104-117, and 202-218 (Mendel I et al, Eur J Immunol. 1995 July; 25(7):1951-9); and the human MOG epitopes 99-107 (FFRDHSYQE; SEQ ID 30); 15-23 (LVGDEVELP; SEQ ID 31); 83-91 (LRIRNVRFS; SEQ ID 32); 120-128 (YWVSPGVLV; SEQ ID 33); and 40-48 (YRPPFSRVV; SEQ ID 34) (Forsthuber T G et al, Journal of Immunology, 2001, 167:7119-7125). In some embodiments, a polynucleotide sequence used in the present invention expresses a contiguous sequence of at least nine amino acids contained in one of the above MOG HLA I epitopes. In other embodiments, a polynucleotide sequence used in the present invention expresses one or more of the above MOG HLA I epitopes.

In another embodiment, a polypeptide is encoded that contains one of more HLA I epitopes of each of myelin basic protein, proteolipid protein and myelin oligodendrocyte glycoprotein. In another embodiment, one of more major HLA I epitopes from each these three proteins is present.

According to one embodiment, said polypeptide part is a contiguous amino acid sequence at least 9, 12, 15, 18, 21, 14, 17, 30, 40, 50, 60, 70, 80, 90, 100, 125, 150, 175 or at least 200 amino acids in length.

According to one embodiment, the expressed nucleic acid sequence is provided as an isolated DNA sequence. By way of non-limiting example, such isolated DNA sequence may be provided as a plasmid, cosmid or mini-chromosome.

According to another embodiment, the expressed nucleic acid is provided as a viral vector. By way of non-limiting example, such viral vector may be an adenovirus, herpes virus, adeno-associated virus or a retrovirus.

According to one embodiment, a lentivirus is provided which comprises an expressed nucleic acid sequence encoding a human autoantigen selected from the group of myelin basic protein, proteolipid protein and myelin oligodendrocyte glycoprotein under transcriptional control of a DC-specific promoter sequence, or the reverse complementary sequence of said expressed nucleic acid sequence.

A preferred lentivirus is a self-inactivating (SIN) lentivirus as described by Lois et al. (Science 2002, 295, 868-872). The SIN lentivirus vector mediated genomic integration of transgenes in HSC supports a constant supply of antigen expressing "steady-state" dendritic cells. The stable antigen presentation by these cells in thymus and periphery in a non-inflammatory condition is likely to tolerize self-reactive T cells and, therefore, prevent disease development or progression. An exemplary, non-limiting type of SIN lentiviruses contain a deletion in U3 region of the 3' LTR, including the TATA box, resulting in the transcriptional inactivation of the LTR in the proviruses in infected cells (Myoshi H et al, J Virol. 1998 October; 72(10):8150-7).

Another aspect of the invention relates to an isolated dendritic cell comprising an expressed nucleic acid sequence according to the invention.

In one embodiment, the dendritic cell comprises an expressed nucleic acid sequence encoding a human autoantigen selected from the group of myelin basic protein; proteolipid protein and myelin oligodendrocyte glycoprotein under transcriptional control of a DC-STAMP promoter sequence.

The invention further encompasses a cell preparation comprising antigen presenting cells obtained from a patient, characterized in that said antigen presenting cells comprise a nucleic acid sequence according to the invention, or a virus according to the invention. The cell preparation is provided for autologous use in prevention or therapy of a demyelinating disease, particularly multiple sclerosis.

In one embodiment, said cell preparation comprises nucleic acid sequences encoding two or three different human proteins selected from myelin basic protein, proteolipid protein and myelin oligodendrocyte glycoprotein.

Also within the scope of the present invention is a pharmaceutical composition for treatment of a demyelinating disease—particularly multiple sclerosis. The composition comprises an isolated dendritic cell comprising an expressed nucleic acid sequence encoding a polypeptide comprising a contiguous sequence of at least nine amino acids contained in a human autoantigen selected from the group of myelin basic protein; proteolipid protein and myelin oligodendrocyte glycoprotein under transcriptional control of a DC-STAMP promoter sequence.

According to yet another aspect of the invention, a dosage regime is provided for use in the therapy of a demyelinating disease, particularly multiple sclerosis, wherein a cell preparation of the invention is administered in conjunction with a drug for partial myeloablative therapy.

According to yet another aspect of the invention, a method of treating multiple sclerosis is provided, comprising providing an isolated dendritic cell according to the invention, to a patient in need thereof.

According to yet another aspect of the invention, a method of treating multiple sclerosis is provided, comprising providing a virus according to the invention, to a patient in need thereof.

In certain embodiments, a method of the present invention is performed in conjunction with partial myeloablative therapy. In other embodiments, a pharmaceutical composition of the present invention is indicated for administration in conjunction with partial myeloablative therapy. Similarly, an ex vivo method of the present invention may, in some embodiments, produce a pharmaceutical composition indicated for administration in conjunction with partial myeloablative therapy. The term "in conjunction with partial myeloablative therapy" includes both simultaneous administration of the pharmaceutical composition and the partial myeloablative therapy, as well as administration of the pharmaceutical composition and the partial myeloablative therapy in temporal proximity. Typically, the pharmaceutical composition and the partial myeloablative therapy will be administered within 48 hours of each other.

The above-mentioned partial myeloablative therapy may preferably comprise administration of a partial myeloablative agent such as busulfan. In other embodiments, one or more of the following agents is administered: alkylating agents (e.g., nitrogen mustards [such as mechloretamine], cyclophosphamide, melphalan and chlorambucil), alkyl sulphonates (e.g., busulphan), nitrosoureas (e.g., carmustine, lomustine, semustine and streptozocine), triazenes (e.g., dacarbazine), antimetabolites (e.g., folic acid analogs such as methotrexate), pyrimidine analogs (e.g. fluorouracil and cytarabine), purine analogs (e.g., fludarabine, idarubicin, cytosine arabinoside, mercaptopurine and thioguanine), vinca alkaloids (e.g., vinblastine, vincristine and vendesine), epipodophyllotoxins (e.g., etoposide and teniposide), antibiotics (e.g., dactinomycin, daunorubicin, doxorubicin, bleomycin, plicamycin and mitomycin), dibromomannitol, deoxyspergualine, dimethyl myleran and thiotepa.

In certain, more specific embodiments, low-dose busulfan may be used. In more specific embodiments, 9 mg/kg or less per day may be used; more preferably 1-9 mg/kg per day. In other embodiments, busulfan is administered at 0.8 mg/kg/day or less, more preferably 0.1-0.8 mg/kg/day.

The strategy presented here is particularly promising for clinical applications, since hematopoietic stem cells isolated from the patient's bone marrow are modified for permanent and continuous output of genetically modified tolerogenic "steady-state" dendritic cells.

The following examples demonstrate the effectiveness of this strategy for inducing myelin oligodendrocyte glycoprotein (MOG)-specific tolerance in EAE. All mice which received HSC transduced with the MOG-expressing lentivirus vector (DC-MOG) were protected from EAE upon immunization (clinical score 0), while all mice that received HSC transduced with a control vector developed EAE. Histological analysis reveled demyelination and extensive inflammation in brain, spinal cord and optical nerve in diseased mice, but not in treated mice. Inflammatory cytokines, including IFN-γ, TNF-α, and IL-17 were almost absent in tolerized mice while they were present at high levels in diseased mice. The results also show that mice which received BM-HSC transduced with DC-MOG displayed efficient deletion of MOG specific T cells and generation of Foxp3+ regulatory T cells. Most importantly, in mice with pre-established EAE, transfer of DC-MOG vector-transduced HSC under partial myeloablative conditions resulted in persistent clinical amelioration of the disease.

Wherever alternatives for single features such as the specific human autoantigens targeted, the length of their polypeptide expressed etc. are laid out herein as "embodiments", it is to be understood that such alternatives may be combined freely to form discrete embodiments of the method or medical indication provided herein.

The following figures and examples, from which further embodiments and advantages can be drawn, are given to illustrate the invention, not to limit it in any way.

EXAMPLES

Materials and Methods

Mice

Figure 1:
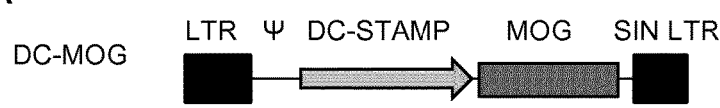
FIG. 1 shows (A:) a schematic representation of a self-inactivating (SIN) lentivirus vector, DC-MOG, expressing full length mouse myelin oligodendrocyte glycoprotein (MOG) from a dendritic cell-specific promoter (DC-STAMP). LTR, long terminal repeat; ψ, packaging signal, and (B:) cell counts for BM-HSC from 5-fluorouracil-treated C57BL/6 donor mice transduced with DC-EGFP and injected into lethally irradiated syngeneic recipient mice. The percentage of EGFP-positive cells (left) and the mean fluorescence intensity (MFI, right) in the cd11c+ and cd11c− cell populations isolated from the spleen of the chimeras is shown at 6 weeks (x-axis: fluorescence, log. scale). The graphs show one of two independent experiments. Each experiment was performed with at least 3 mice per group. Bars represent mean values+SD.
Figure 1:
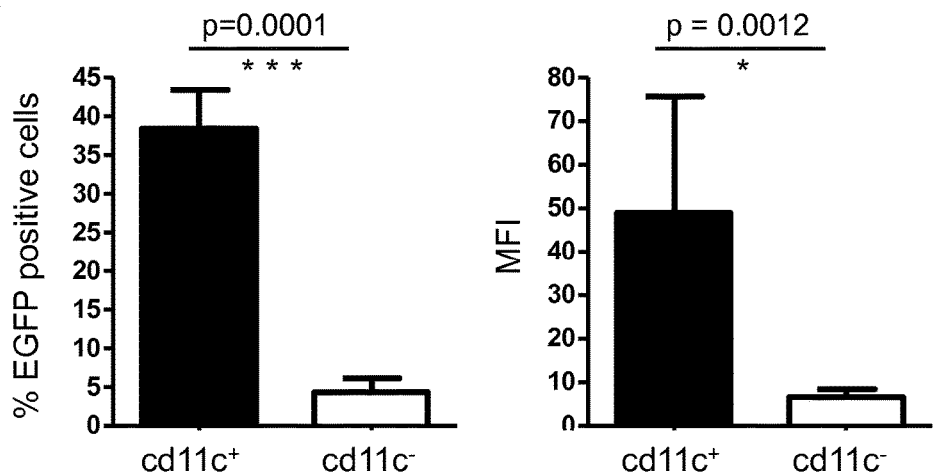

C57BL/6 (CD45.1 and CD45.2) and 2D2 (CD45.2) mice were maintained and bred at the animal facility of the Institute of Virology, University of Zurich. 2D2 mice have transgenic Va3.2/Vβ11 TCRs specific for myelin oligodendrocyte glycoprotein peptide (MOG)$_{35-55}$.

SIN Lentivirus Vectors

SIN lentivirus vectors which express EGFP (DC-EGFP) or ovalbumin (OVA, DC-OVA) fused to the transmembrane domain of the human transferrin receptor (htfr), respectively, have been described previously (Dresch et al., J. Immunology 2008, 181; 4495-4506). SIN lentivirus vector DC-MOG expresses the full length mouse MOG ORF (see sequence protocol: SEQ ID 01) under control of the DC-STAMP promoter (see sequence protocol: SEQ ID 02) and was constructed as follows: The MOG sequence was amplified by PCR with primers 38 (5'gtaccggtgccaccatggcctgtttgtggagctt3', SEQ ID 03) and 39 (5'aggaattcccaggaagacacaac-catcac3' SEQ ID 04 from a plasmid (pFLC1, ImaGenes GmbH, Berlin, Germany) containing the mouse MOG cDNA. The PCR product was digested with AgeI and EcoRI and inserted between the AgeI and EcoRI sites of DC-EGFP. Vector stocks were produced and titers determined exactly as described in Dresch et al., 2008.

Bone Marrow Chimeras

Bone marrow (BM) cells of at least 6-wk-old female C57BL/6 or 2D2 mice were harvested 4 days after i.v. injection of 5 Fluorouracil (150 mg/kg body weight). The cells were prestimulated for 2 days in serum-free hematopoietic stem cell expansion medium (Stemline, Sigma-Aldrich) supplemented with penicillin-streptomycin and a growth factor mixture containing human IL-6 (25 ng/ml), murine IL-3 (10 ng/ml), and murine stem cell factor (50 ng/ml). Cells were transduced by spin infection (300×g; 2 h; 32° C.) with cell free stocks of SIN lentivirus vector (multiplicity of infection MOI=45) in the presence of protamine sulfate (4 µg/ml). After the transduction, 1-3×10$^6$ cells/mouse were injected i.v. in lethally irradiated (11 Gy) C57BL/6 recipients. The chimeras were treated with neomycin for 3 weeks after transplantation.

Induction of EAE

Preventive model.

At 8 weeks after transplantation, bone marrow chimeras were injected s.c. with 0.1 mg of MOG peptide (ProSpec, Rehovot, Israel; catalogue ID PRO-371) emulsified in complete Freund's adjuvant supplemented with 5 mg/ml Mycobacterium tuberculosis in a total volume of 200 µl. The animals were subsequently injected i.p. with 300 ng pertussis toxin; this injection was repeated 48 h later. Mice were monitored daily for neurological signs of EAE and scored as follows: 0, no clinical sign; 1, limp tail; 1.5, limp tail and hind limb weakness; 2.0, unilateral partial hind limb paralysis; 2.5, bilateral partial hind limb paralysis; 3.0, complete bilateral hind limb paralysis (animals are sacrificed at this stage).

Curative Model.

EAE was induced in untreated 6 week-old female C57BL/6 mice as described above. The animals were scored daily for signs of disease and conditioned with 20 mg/kg of busulfan on days 4 and 5 after the first symptoms developed. Vector transduced BM-HSC (1-3×10$^6$ cells/mouse) were injected i.v. 2 days after the second busulfan treatment.

CNS Histopathology

Brain and optical nerve were fixed in 4% formaldehyde and embedded in paraffin. Spinal cord was left in the vertebrae and, after fixation, decalcified for 2 weeks with 25% EDTA before paraffin-embedding. For histochemical and immunohistochemical staining, 3 mm thick slides were deparaffinated with xylol and alcohol and either stained with hematoxylin and eosin or processed as follows: For assessing demyelination, the slides were incubated in luxol fast blue and counterstained with crystal violet. For immunohistochemical staining, the slides were stained with the following antibodies: rat anti-mouse anti-Mac3 (macrophages; 1:10; BD Pharmingen), mouse anti-SMI 32 (neurofilament; 1:400; Abcam, Cambridge, UK), or rabbit anti-mouse CD3 (T-cells; 1:100; Ventana Medical Systems, Inc., Tucson, Ariz., USA).

Bone Marrow Derived Dendritic Cells and In Vitro T Cell Proliferation Assay

Bone marrow cells from chimeras were extracted from femur and tibia at 6-8 weeks after EAE induction. The cells were then cultured in 6 well plates at 37° C. in RPMI 1640 medium supplemented with 10% fetal bovine serum (FBS), 1% penicillin-streptomycin, 0.1 mM Hepes and DC differentiation factor GMC-SF. At day 6, 2D2 T cells labeled with 2.5 µM CFSE (carboxyfluorescein diacetate succinimidyl ester) were added to the BM culture, and proliferation was analyzed by flow cytometry 3 days later.

Cytokine Analysis

Cytokines were measured by in vitro splenocyte stimulation. For this, splenocytes were cultured in 6 well plates (1×10$^7$ cells per well) in DMEM supplemented with 10% FBS, 1% penicillin-streptomycin, 0.1 mM Hepes, 2 mM L-glutamine, 0.01 mM non-essential amino acids. Splenocytes were stimulated with MOG$_{35-55}$ peptide (5 µg/ml in PBS; PROSPEC, Israel). For a positive control, splenocytes were stimulated with 5 µg/ml of PMA; for a negative control, splenocytes were cultured without peptide. The supernatant was collected at 12, 24, 48 and 72 h after stimulation and stored at −80° C. The cytokines (GM-CSF, IFN-γ, IL-4, IL-5, IL-6, IL-17, TNF-α) in the supernatants were measured by flow cytometry using the Mouse Th1/Th2 10plex kit (Bender MedSystems, Vienna, Austria) according to the protocol provided by the manufacturer. Cytokines were also measured in the supernatant of CNS. For this, the brain and spinal cord were homogenated in a final volume of 1 mg/µl, centrifuged at 1'200 rpm for 5 min, and the supernatant was analyzed directly or stored at −80° C. for later analysis.

Antigen Specific Tolerance Induction by DC-MOG or DC-OVA Vector-Transduced BM-HSC To determine antigen specificity, cytokine responses were measured as described above, except that splenocytes were isolated from chimeras, which at 8 weeks after transplantation of vector-transduced BM-HSC, were immunized simultaneously with MOG and OVA antigen as follows: 0.1 mg of MOG peptide (ProSpec) and 0.1 mg of OVA protein (NeoMPS, Strasbourg, France) was emulsified in complete Freund's adjuvant supplemented with 5 mg/ml Mycobacterium tuberculosis in a total volume of 200 µl per mouse and injected s.c. The animals were subsequently injected i.p. with 300 ng pertussis toxin (Sigma Aldrich); this injection was repeated 48 h later. Splenocytes were isolated when the animals reached score 3 or, for protected mice, or 14 days after the last of the diseased animals was analyzed.

Isolation of CD4 T Cells from Brain

To analyze the frequency of CD4 T cells in the brain, the organ was homogenized in DMEM and centrifuged at 1'200 rpm for 10 min at room temperature. The pellet was suspended in 5 ml of 37% percoll in PBS, and 2.5 ml of 70% percoll in PBS was added carefully. The samples were centrifuged at 600 g for 20 min at room temperature, and the leucocytes in the interface were harvested, washed several times with PBS and analyzed by flow cytometry.

FACS Analysis

Donor engraftment and chimerism was assessed at 6-8 weeks after transplantation by cytometric analysis of CD45.1 versus CD45.2 in the thymus using APC-conjugated anti-CD 45.1 (A20; BD Biosciences) and PE-conjugated anti-CD45.2 (104; eBioscience), respectively. For analysis of DCs and DC-specificity of EGFP transgene expression, the following antibodies were used: biotin-conjugated anti-CD3 (145-2C11; BD Biosciences), PE-conjugated anti-CD11b (M1/70; BD Biosciences), PerCP-conjugated anti-CD45 (RA3-6120.1; BD Biosciences), PE-conjugated anti-I-A[b], (AF6-120.1; BD Biosciences), Biotin-conjugated anti-Ly-6G/Ly-6C (Gr-1; RB6-8C5, BD Biosciences), FITC-conjugated anti-CD3 (145-2C11, BD Biosciences), APC-conjugated anti-CD11c (N418, BD Biosciences), PerCP-conjugated anti-cD11c (N418, BD Biosciences), PerCP-conjugated anti-CD8 (53-6.7, BD Biosciences), PE-conjugated anti-CD19 (6D5, BD Biosciences), PerCP/Cy5.5-conjugated anti-CD103 (2E7, BD Biosciences), PerCP-conjugated anti-F4/80 (BM8, BD Biosciences), PE-conjugated streptavidin (BD Biosciences), PE/Cy7-conjugated anti-CD4 (GK1.5, eBioscience), PE/Cy5-conjugated anti-NK1.1 (PK136, eBioscience), and APC-conjugated anti-NK (Dx5, eBioscience). T cells, including Tregs and 2D2 T cells, were analyzed with the following antibodies: FITC-conjugated anti-Vα 3.2 (RR3/16, BD Biosciences), PE-conjugated anti-Vβ 11 (KT11, BioLegend), APC-conjugated anti-CD4 (RM4-5, BD Biosciences), PE-conjugated anti-CD152 (UC10-4B9, BioLegend), APC-conjugated anti-Foxp3+ (APC Anti-Mouse/Rat Foxp3 staining Set Kit, eBioscience), APC-conjugated anti-CD25 (PC61.5, eBioscience), APC-conjugated anti-CD69, H1.2F3, BD Biosciences), APC-conjugated anti-CD44 (IM7, eBioscience), APC-conjugated anti-CD62L (MEL-14, eBioscience), FITC-conjugated anti-CD3 (145-2C11, BD Biosciences), APC-conjugated anti-CD4 (RM4-5, BD Biosciences, PerCP-conjugated anti-CD8 (53-6.7, BD Biosciences).

Statistical Analysis

Statistical analysis was performed by one-tailed (FIG. 5, left panel) or two-tailed (all other statistical analyses) t-test with GRAPHPAD PRISM version 5.02 software. Data are presented as mean values+/−SD, unless otherwise stated. Differences were considered significant when p values were below 0.05.

RESULTS

Example 1

SIN Lentivirus Vector-Mediated DC-Specific Antigen Expression

SIN lentivirus vectors expressing full length murine MOG were constructed from the DC-specific STAMP promoter (DC-MOG; FIG. 1A). Control vectors expressing EGFP (DC-EGFP) or a membrane targeted OVA (DC-OVA) from the DC-STAMP promoter have been described previously (Dresch et al. 2008). Vector-mediated MOG expression was demonstrated by immunofluorescence analysis of vector-transduced bone marrow derived DCs (BM-DC) (not shown). Vector encoded MOG was functional as shown by T cell proliferation assays using vector transduced BM-DCs and CD4+ T cells isolated from 2D2 mice, which are transgenic for a T cell receptor (V$\alpha$3.2 and V$\beta$11 chains) that recognizes the MOG$_{35-55}$ peptide (not shown).

The transcriptional specificity conferred by the DC-STAMP promoter was previously demonstrated (Dresch et al., 2008) and was confirmed here as follows: Bone marrow derived hematopoietic stem cells (BM-HSC) from C57BL/6 donor mice were transduced with DC-EGFP and then transplanted into lethally irradiated syngeneic recipient mice. At 6 weeks after transplantation of DC-EGFP transduced BM-HSC, EGFP fluorescence was detected in more than 35% of cd11c$^+$ cells, while less than 5% of cd11c$^-$ cells were EGFP positive. Moreover, the mean fluorescence intensity (MFI) in the 5% cd11c$^-$ cells was significantly lower than that in EGFP positive, cd11c$^+$ cells (FIG. 1B). Chimerism in the spleen was at least 96% (not shown).

Example 2

Figure 2:
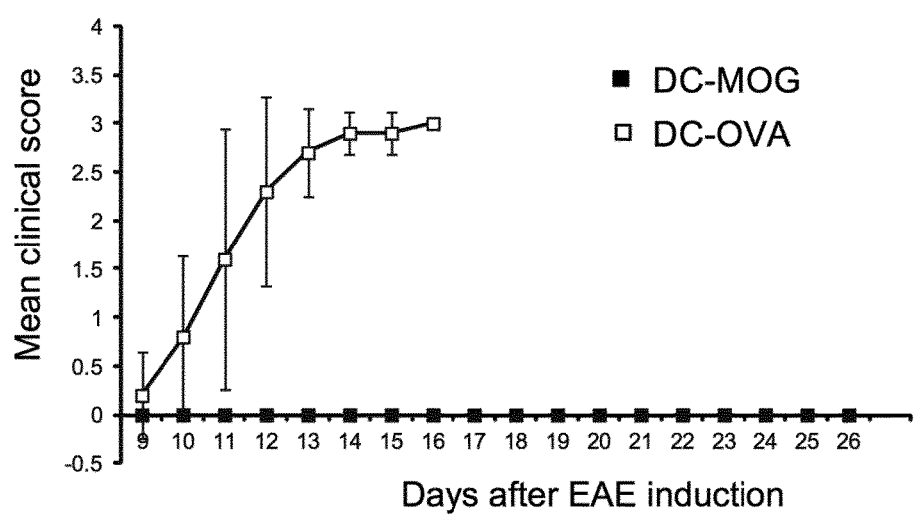
FIG. 2 shows (A:) Clinical scores (mean values +/−SD) of MOG-immunized C57BL/6 mice transplanted with BM-HSC transduced with DC-MOG or DC-OVA vectors. The graph shown represents 1 out of 3 independent experiments with 5 mice per group; (B:) Bone marrow DCS were prepared from DC-MOG chimeras at 13 weeks after transplantation. For the DC-OVA group, BM-DCs were prepared when the animals were killed after they reached score 3 of EAE. After 3 days in culture, the percentage of proliferating 2D2 T cells was determined by flow cytometry. Dilution of CFSE indicates proliferation of the T cells. Histograms shown are from individual mice but the data is representative for at least 3 animals analyzed from each of the two different groups.
Figure 2:
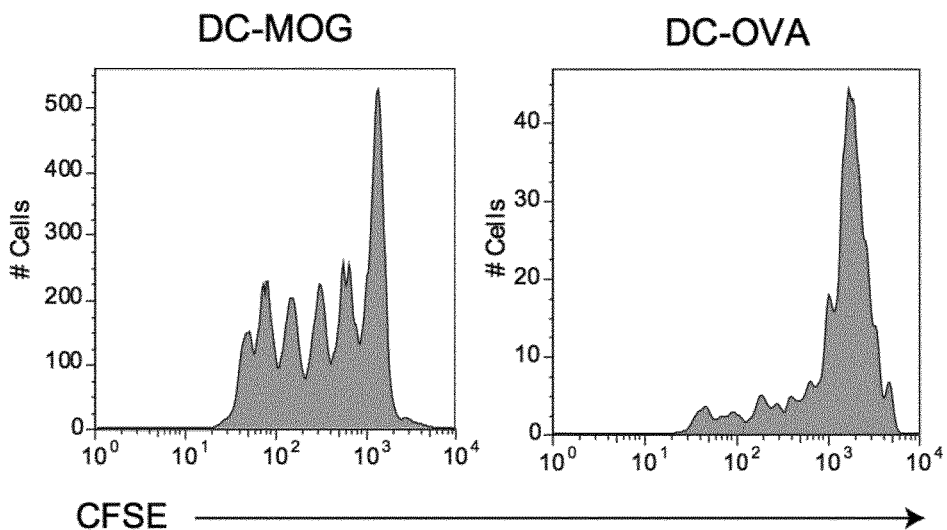

Transplantation of DC-MOG Vector-Transduced BM-HSC Protects Mice from EAE Disease Next, lethally irradiated C57BL/6 mice were transplanted with DC-MOG or control vector (DC-EGFP or DC-OVA) transduced BM-HSC from syngeneic donors. After 8 weeks, EAE was induced, and clinical signs of disease were assessed twice per day. FIG. 2A shows that the control mice started to develop EAE at around day 10 after induction (mean onset day 10.5+1.3), and that all of the animals reached clinical score 3 within less than one week after disease onset. Importantly, none of the mice that received DC-MOG transduced BM-HSC developed any neurological symptoms (clinical score 0). The DC-MOG chimeras did not develop EAE for at least 5 weeks after induction and continued to produce MOG expressing DCs for at least 13 weeks after reconstitution of the immune system, as demonstrated by the proliferation of 2D2 T cells in presence of BM-DCs isolated from these animals (FIG. 2B). In three independent experiments, none of the DC-MOG chimeras developed any signs of clinical symptoms, while all chimeras that received control vector-transduced BM-HSC progressed to clinical score 3, at which point they were sacrificed.

Figure 3:
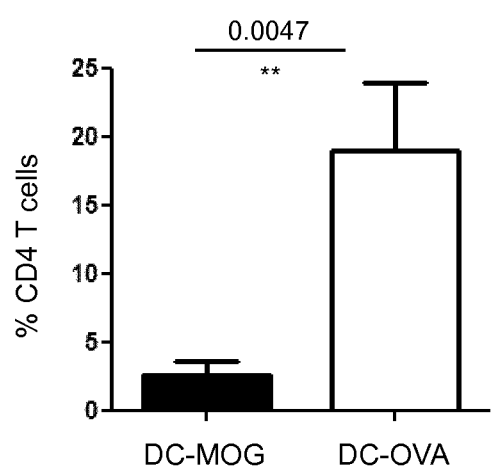
FIG. 3 shows % CD4 T cells in the CNS of DC-MOG and DC-OVA chimeras. Bars represent mean values+SD from 1 out of 2 independent experiments with 5 and 3 mice per group, respectively.

Histological analysis of the tolerized animals did not reveal any evidence of CNS pathology. By contrast, chimeras that received control vector-transduced BM-HSC showed extensive multifocal inflammatory infiltrates and demyelination in brain (not shown), optical nerve and spinal cord. Moderate to severe demyelination and axonal damage was observed in the affected tissues, as determined by staining of myelin and neurofilament, respectively. The inflammatory process involved massive infiltration of macrophages and T cells. The frequency of CD4 T cells in the CNS of diseased animals was more than 7-fold higher than in protected mice (FIG. 3). In the brain, mainly the meninges and the white matter, rarely the gray matter was involved (not shown). In the spinal cord the intensity of the demyelination and inflammatory process increased to the caudal parts (not shown).

Figure 4:
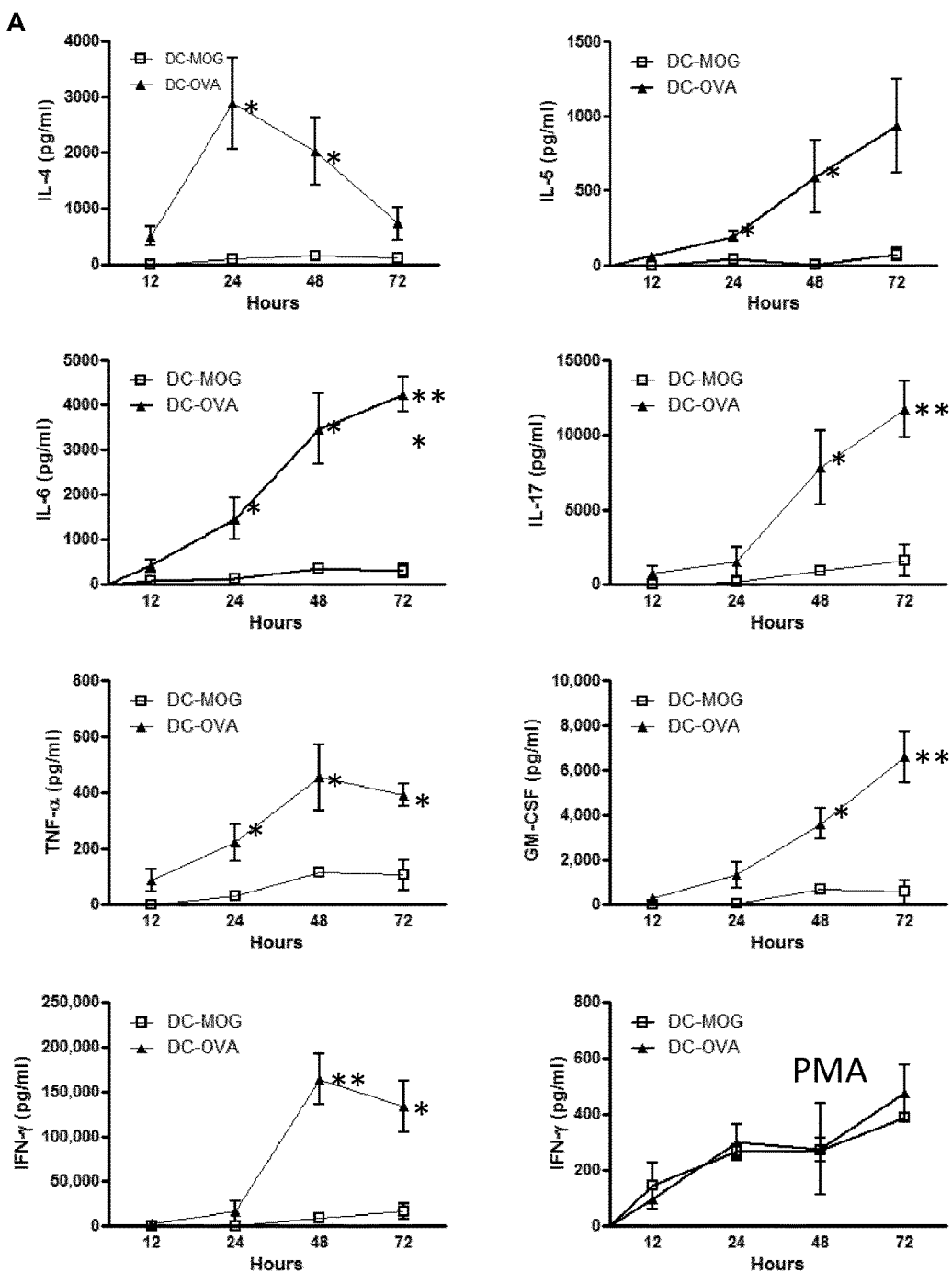
FIG. 4 (A) Splenocytes were isolated from DC-MOG and DC-OVA chimeras after the animals reached score 3 of EAE or, for the protected mice, 14 days after EAE induction, and were re-stimulated in vitro with MOG35-55 peptide. Concentrations of the indicated cytokines were measured after 12, 24, 36, and 48 h. IFN-γ concentrations were determined also upon non-specific stimulation with PMA. (B) Concentrations of the indicated cytokines in CNS homogenates. Data represent mean values+SD from 1 out of 2 independent experiments with at least 3 mice per group.
Figure 4:
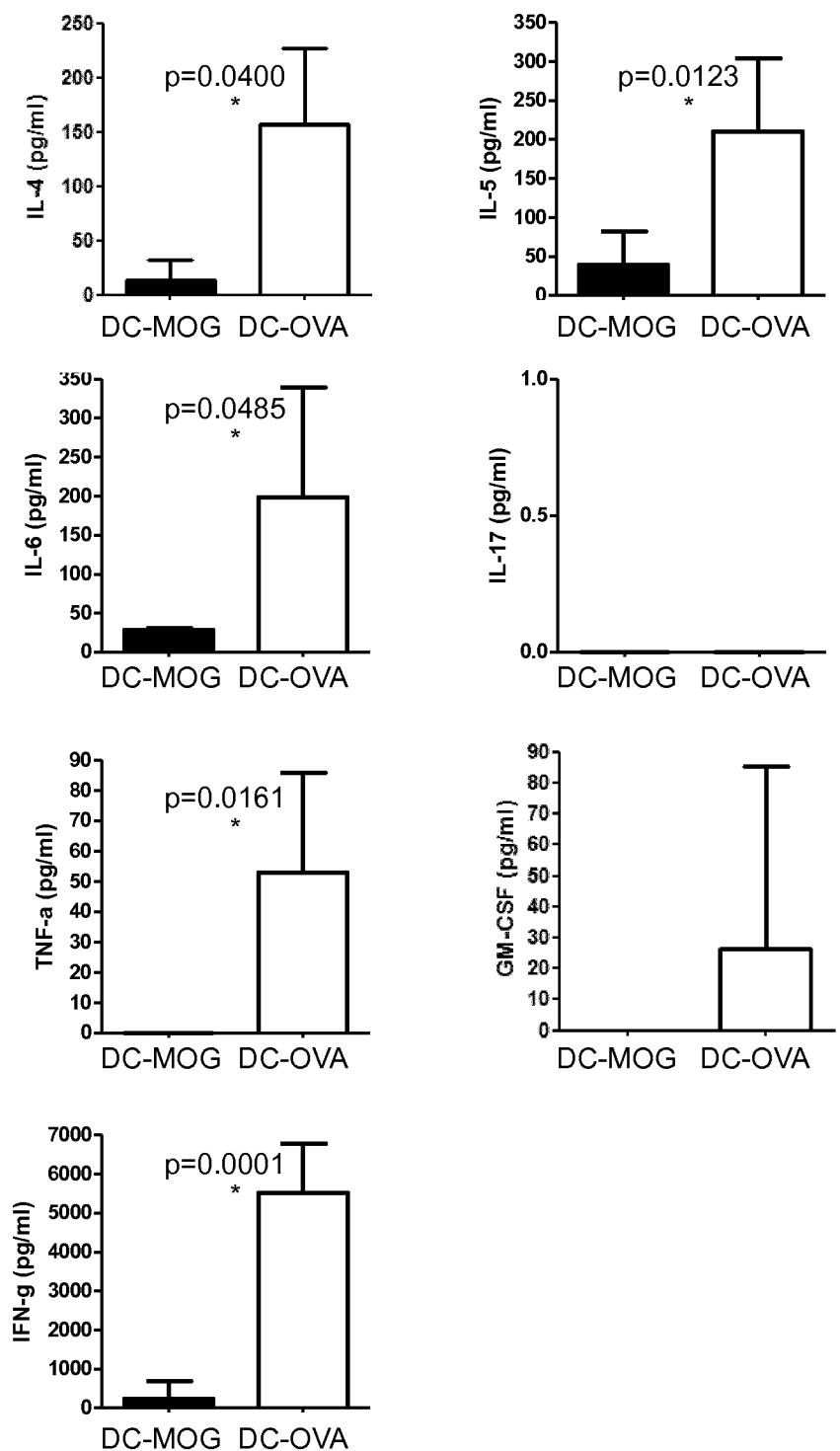

Cytokine production patterns in spleen and CNS of diseased and protected mice were analyzed. As shown in FIG. 4A, concentrations of Th2 cytokines (IL4, IL-5, IL-6) and inflammatory cytokines (IL-17, TNF-$\alpha$, GM-CSF, and IFN-$\gamma$) in spleen of diseased DC-OVA control vector transduced BM-HSC chimeras were much higher than those in protected DC-MOG chimeras. A general impairment of cytokine production in the protected mice can be ruled out, as IFN-$\gamma$ production was comparable in splenocytes from diseased and protected mice upon non-specific stimulation with PMA (FIG. 4A). The cytokine pattern observed in the CNS was comparable to that in the spleen, except that in this tissue IL-17 was undetectable in both protected (DC-MOG) and diseased (DC-OVA) animals (FIG. 4B).

Figure 5:
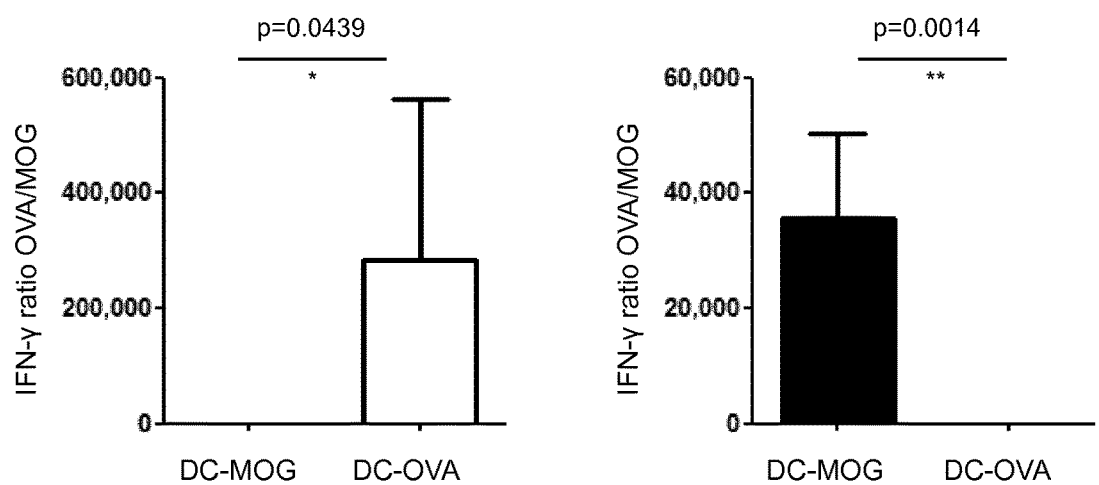
FIG. 5 shows antigen specific tolerance induction by DC-MOG or DC-OVA vector-transduced BM-HSC. Splenocytes isolated from chimeras simultaneously immunized with MOG and OVA peptides were stimulated with either MOG or OVA peptide, and IFN-γ concentrations were measured. The bars represent mean ratios+SD of IFN-γ concentrations in MOG peptide stimulated splenocytes divided by IFN-γ concentrations in OVA peptide stimulated splenocytes (MOG/OVA, left panel) or vice versa (OVA/MOG, right panel). The data shown represents 1 out of 2 independent experiments with 4 mice each.

Specificity of tolerance was demonstrated by immunizing DC-MOG or DC-OVA vector transduced BM-HSC chimeras simultaneously with OVA and MOG peptide and measuring IFN-$\gamma$ production by splenocytes. As expected, IFN-$\gamma$ responses in the DC-MOG tolerized chimeras were detected upon stimulation with OVA peptide, but not upon stimulation with MOG peptide, while cytokine responses in DC-OVA tolerized chimeras were obtained upon stimulation with MOG peptide, but not upon stimulation with OVA peptide (FIG. 5).

Figure 6:
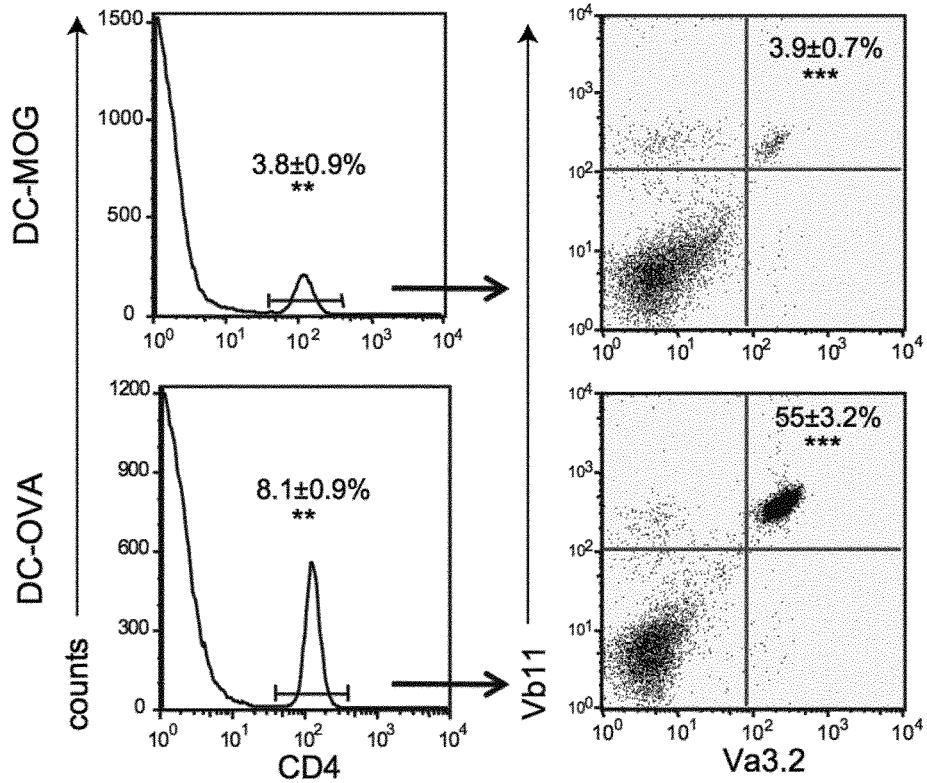
FIG. 6 shows central and peripheral deletion of MOG35-55—specific T cells in DC-MOG chimeras. Lethally irradiated C57BL/6 cells were transplanted with DC-MOG or DC-OVA vector-transduced BM-HSC from 2D2 mice. After 6-8 weeks, CD4 T cells and 2D2 T cells (Va3.2+ and Vb11+) gated on CD4 T cells were quantified by flow cytometry. A. Percentage+SD of CD4 T cells (left panels) and 2D2 T cells (right panels) in spleen are indicated and represent 1 out of 3 independent experiments with 6 mice per group. The histograms represent individual animals. B. Absolute numbers of CD4 T cells (upper panels) and 2D2 T cells (lower panels) in spleen and thymus. Bars represent values+SD from 1 out of 3 independent experiments with 6 mice per group.
Figure 6:
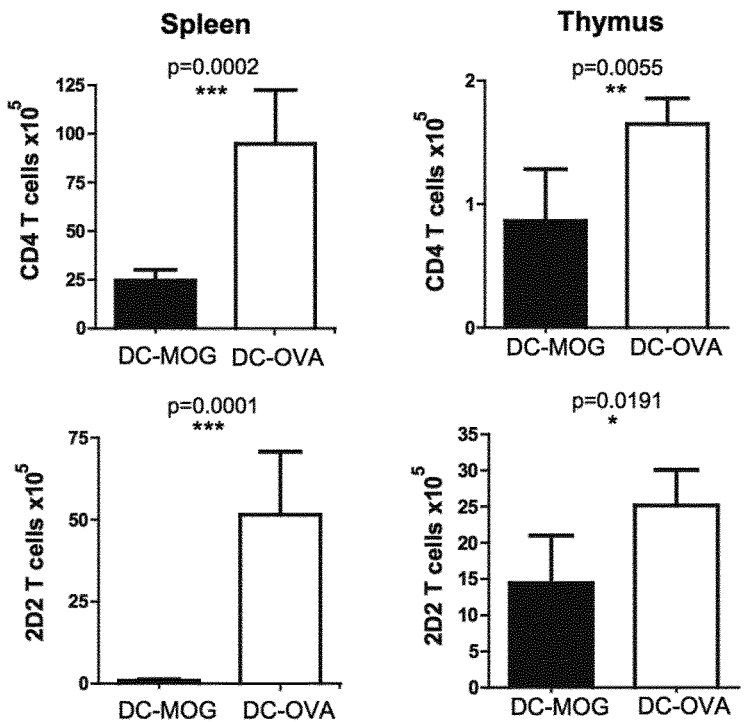
Figure 7:
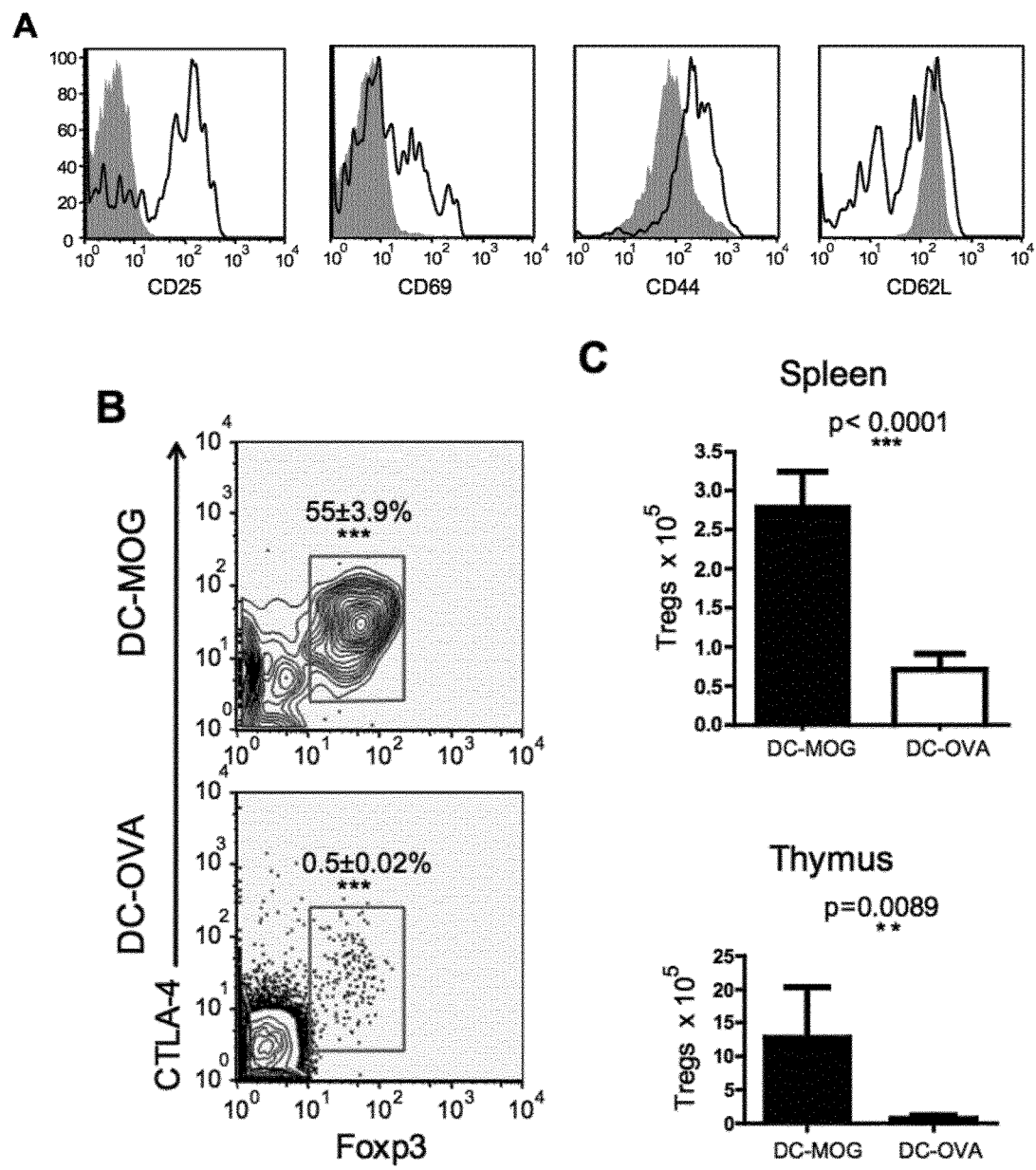
FIG. 7 shows activation/regulatory status of 2D2 T cells. A. CD25, CD69, CD44, and CD62L were analyzed on 2D2 T cells from spleen of DC-MOG (open histograms) and DC-OVA (shaded histograms) chimeras by flow cytometry. Histograms show representative data from individual mice. B and C. 2D2 T cells from DC-MOG and DC-OVA chimeras were analyzed also for regulatory T cell phenotype (CTLA-4+ and Foxp3+). Percentages+SD of CTLA-4 and Foxp3 positive cells (Tregs) indicated in B represent 1 out of 2 independent experiments with 6 mice per group. The histograms represent individual animals. Absolute numbers of Tregs+SD in spleen and thymus are shown in C.

Transplantation of DC-MOG Vector Transduced BM-HSC Results in the Depletion of MOG-specific T Cells and the Induction of Regulatory T Cells To investigate possible mechanisms of tolerance induction, lethally irradiated C57BL/6 mice were transplanted with DC-MOG or DC-OVA vector transduced BM-HSC isolated from 2D2 donors, and MOG-specific 2D2 T cells from the chimeras were quantified 6-8 weeks later. The results are shown in FIG. 6 and can be summarized as follows: 2D2 T cells were largely depleted in chimeras that received DC-MOG vector transduced BM-HSC, compared to animals that received control vector (DC-OVA) transduced BM-HSC. In the DC-MOG treated mice only approximately 4% of the CD4+ T cells in the spleen contained the V$\alpha$3.2/V$\beta$11 TCR, while approximately 55% of the DC-OVA control vector treated mice contained this MOG$_{35-55}$ specific TCR (FIG. 6A). The total numbers of 2D2 T cells in spleen of protected mice were also much lower than in diseased mice (FIG. 6B). The depletion of 2D2 T cells in protected mice was less pronounced in thymus than in spleen but was nevertheless significant (FIG. 6B). Further analysis of the remaining 2D2 T cells in spleen revealed an antigen-experienced phenotype in DC-MOG chimeras, characterized by up-regulation of CD25, CD44 and CD69, and slight down regulation of CD62L (FIG. 7A). We also analyzed the remaining 2D2 T cells for regulatory T cell ($T_{reg}$) phenotype and found that in spleen of DC-MOG treated mice more than 50% of the remaining 2D2 T cells were CTLA-4 and Foxp3 positive; less than 1% of the 2D2 T cells isolated from DC-OVA treated mice showed a $T_{reg}$ phenotype (FIG. 7B). The absolute numbers of $T_{reg}$ 2D2 T cells in thymus and spleen of DC-MOG and DC-OVA chimeras is shown in FIG. 7C.

Transplantation of DC-MOG Vector-Transduced BM-HSC Ameliorates Established EAE

Figure 8:
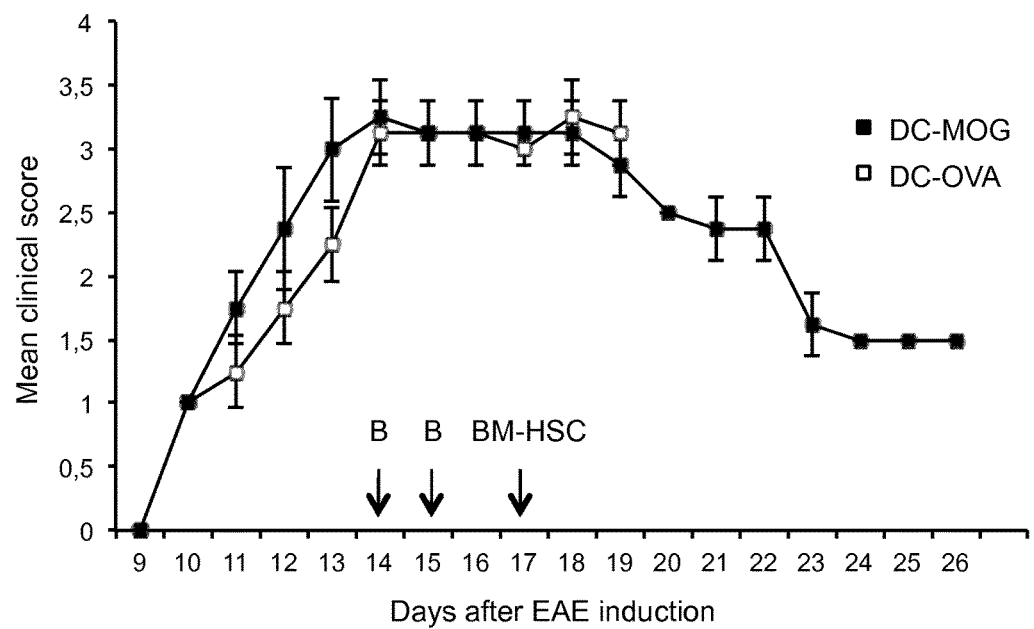
FIG. 8 shows the effect of gene therapy on the development of pre-established EAE (curative protocol). Untreated C57BL/6 mice were immunized with MOG peptide. On days 4 and 5 after the first symptoms of EAE have developed, the animals were conditioned with busulfan (B), and 2 days later, transplanted under partial myeloablative conditions with DC-MOG or DC-OVA transduced BM-HSC from syngeneic mice. The graph represents 1 out of 2 independent experiments and shows clinical scores +SD from at least 4 mice per group.

We investigated whether the strategy of transplanting SIN-lentivirus vector-transduced BM-HSC that give rise to MOG expressing DCs can be effective also in treating established EAE. For this curative protocol, EAE was established in untreated mice by immunization with MOG peptide exactly as described for the preventive protocol. On days 4 and 5 after the first symptoms were observed, the animals were conditioned with low dose busulfan and transplanted with DC-MOG or DC-OVA transduced BM-HSC as described in Materials and Methods. In two independent experiments, clinical improvement was observed in all animals of the DC-MOG group and was maintained over the entire period of the experiment (FIG. 8). By contrast, no clinical improvement was observed in the control group (DC-OVA), and the animals were killed when clinical score 3 was maintained for more than two days after transplantation.

These results indicate that transplantation of self BM-HSC transduced with DC-MOG is a promising approach to treat EAE/MS. This strategy can be potentially useful in treating other autoimmune diseases in which the self-antigens involved in the development of the patology are known.

The invention claimed is:

1. A method of treating, reverting or halting the progression of multiple sclerosis comprising: administering a nucleic acid molecule to a patient in need thereof, said nucleic acid molecule comprising a sequence having an open reading frame encoding a polypeptide, said polypeptide comprising at least one amino acid sequence selected from the group consisting of
SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, and SEQ ID NO. 34;
wherein SEQ ID NOs. 22-25 are myelin basic protein (MBP) HLAI epitopes, SEQ ID NOs. 26-29 are proteolipid protein (PLP) HLAI epitopes, and SEQ ID NOs. 30-34 are myelin oligodendrocyte glycoprotein (MOG) HLAI epitopes; and
wherein said open reading frame is under transcriptional control of a DC-STAMP promoter sequence.

2. The method of claim 1, wherein the nucleic acid molecule is comprised within a virus.

3. The method of claim 2, wherein the step of administering is performed together with partial myeloablative therapy, optionally wherein said therapy comprises administration of busulfan.

4. The method of claim 1, wherein the nucleic acid molecule is comprised within an isolated dendritic cell, said isolated dendritic cell optionally transduced with a lentivirus or lentivirus vector comprising said nucleic acid molecule.

5. The method of claim 4, wherein the step of administering is performed together with partial myeloablative therapy, optionally wherein said therapy comprises administration of busulfan.

6. The method of claim 1, wherein the nucleic acid molecule is comprised within an antigen presenting cell obtained from a patient.

7. The method of claim 1, wherein the nucleic acid molecule is comprised within an antigen presenting cell, said antigen presenting cell obtained from a patient, wherein the cell comprises nucleic acid sequences encoding two or three different human proteins selected from myelin basic protein, proteolipid protein and myelin oligodendrocyte glycoprotein.

8. The method of claim 1, said nucleic acid molecule comprised in a pharmaceutical composition comprising a first isolated dendritic cell comprising a first sequence having an open reading frame encoding a first polypeptide said open reading frame under transcriptional control of a DC-STAMP promoter sequence, said first polypeptide comprising at least one amino acid sequence selected from SEQ ID NO. 22, SEQ ID NO. 23, SEQ ID NO. 24 and SEQ ID NO. 25 of human myelin basic protein;

a second isolated dendritic cell comprising a second sequence having an open reading frame encoding a second polypeptide said open reading frame under transcriptional control of a DC-STAMP promoter sequence, said second polypeptide comprising at least one amino acid sequence selected from SEQ ID NO. 26, SEQ ID NO. 27, SEQ ID NO. 28 and SEQ ID NO. 29 of human proteolipid protein; and a third isolated dendritic cell comprising a third sequence having an open reading frame encoding a third polypeptide said open reading frame under transcriptional control of a DC-STAMP promoter sequence, said third polypeptide comprising at least one amino acid sequence selected from SEQ ID NO. 30, SEQ ID NO. 31, SEQ ID NO. 32, SEQ ID NO. 33, and SEQ ID NO. 34 of human myelin oligodendrocyte glycoprotein.

9. The method of claim 8, said first isolated dendritic cell transduced with a lentivirus or lentivirus vector, said lentivirus or lentivirus vector comprising said first sequence;

said second isolated dendritic cell transduced with a lentivirus or lentivirus vector, said lentivirus or lentivirus vector comprising said second sequence;

said third isolated dendritic cell transduced with a lentivirus or lentivirus vector, said lentivirus or lentivirus vector comprising said third sequence.

10. The method of claim 1, wherein said sequence having an open reading frame encodes myelin basic protein, proteolipid protein or myelin oligodendrocyte.

11. The method of claim 1, wherein said nucleic acid is comprised within a bone marrow derived haematopoietic stem cell.

* * * * *

SEQUENCE LISTING

<160> NUMBER OF SEQ ID NOS: 39

<210> SEQ ID NO 1
<211> LENGTH: 748
<212> TYPE: DNA
<213> ORGANISM: Homo sapiens

<400> SEQUENCE: 1

```
atggcctgtt tgtggagctt ctcttggccc agctgcttcc tctcccttct cctcctcctt      60
ctcctccagt tgtcatgcag ctatgcagga caattcagag tgataggacc agggtatccc     120
atccgggctt tagttgggga tgaagcagag ctgccgtgcc gcatctctcc tgggaaaaat     180
gccacgggca tggaggtggg ttggtaccgt tctcccttct caagagtggt tcacctctac     240
cgaaatggca aggaccaaga tgcagagcaa gcacctgaat accggggacg cacagagctt     300
ctgaaagaga ctatcagtga gggaaaggtt acccttagga ttcagaacgt gagattctca     360
gatgaaggag gctacacctg cttcttcaga gaccactctt accaagaaga ggcagcaatg     420
gagttgaaag tggaagatcc cttctattgg gtcaaccccg gtgtgctgac tctcatcgca     480
cttgtgccta cgatcctcct gcaggtctct gtaggccttg tattcctctt cctgcagcac     540
agactgagag gaaaacttcg tgcagaagta gagaatctcc atcggacttt tgatcctcac     600
ttcctgaggg tgccctgctg gaagataaca ctgtttgtta ttgtgcctgt tcttggaccc     660
ctggttgcct tgatcatctg ctacaactgg ctgcaccgaa gactggcagg acagtttctt     720
gaagagctaa gaaaccccett ttgagtga                                        748
```

<210> SEQ ID NO 2
<211> LENGTH: 1756
<212> TYPE: DNA
<213> ORGANISM: Homo sapiens

<400> SEQUENCE: 2

```
gcatcgttct gtgttgtctc tgtctgacgt ggttctgtat tgtctgaaaa tagcggcctg      60
cctctaagga agaaataatt ctgcatagaa atcacttgtg accttgggct ccaaagtcaa     120 ctcttttcctg gacccataat ctatcatttc tgtctcatag cttcaacttg ccctcaacag     180
attaaattgc atttaactga atcaaaatga ataaaactcc caaaatttca atgaagaaaa     240
aaattgtgga tgcagatttt ggaattacaa atctacaact gaatgaacca attcattaaa     300
```

```
cctgccctgc cttcaaaata tgtgtatgca tgtatatata aatagataca tatatgagtg      360
tatatatata tatgtgcgtg tgtgtgtgtg tgtgtgtgtg tagacatata tatttgtttc      420
tcttataaat tacaagtctt ttaaaatcag aatttggaat tttatttggt ttttacatct      480
ctcagtgtct aagcatttta aagaatttca acaaatacct gttgatctat cagttatttc      540
caaatgaata cttccaaaat tttagggaga caggaaaact gttggcattg ttgaagagtc      600
cagacagcac atatgaaata aataaaagaa acattttgag aagagagaat atcgataatt      660
taatcaggag attaattgta aatgtcactt cttaatgtgt aggtgtgtct ttgaaattct      720
gacaagcttg caaatgcata tgggtaataa ttttgaaaat atgacttgat accttgacat      780
ttctatagct tctcactcag tcatatgatc aaaattgtta ttagtaataa tatttaaggc      840
aacatccttc ttagagacat ttgaatttgc ctagaaattg taaatttttt tgcttttaaa      900 ttttttttctt attagatatt ttcttcattt acatttcaaa tgctatcccc aaagtcccct    960
ataccctctc ccagacctgc tctccaaccc acccactccc gcttcctggc cctggcgttc    1020
ccctgtacta gagcgtatga tcttcgcgag accaagggcc tctcctccca atgatggccg    1080
actaagccat ttaacataaa aactttcaca gactgattga ctggctttat acaaagtttt    1140
tgagacttgt ctacatcttt tgaagaacaa tggtcttttc agccagagaa gtaaacttct    1200
aagctgataa gtactatgtg tgcgttggaa tcacctagta gcttcagagc tatgggctca    1260
tccagaaatc tgacttttca gctgtgggtg gggcctgagg gcaagaccaa tctgccctcc    1320
ccatggctgg ggtgagcagg gaggaaaaag ggaaggaaga gaatgggggg gggtcctcat    1380
ttctacaact cattgttttg aaaatatcct attatgttat ttcctagggt taatgtctaa    1440
ggaaagtgct ggaatgaaac ctgtggctcc tttttccagt ttttacccct gatgacatta    1500
aataacttcg tcactttgtg gaggaaatga gaagattgat tcagggtgat gtggcccacc    1560
taccttctca tgtccagttc cccttttccct gacctatatt aagcctacga gcttccagaa    1620
gggtgtgctt tgtgcttgtg gaggaaccta agcggaactt gtaagtaaac tttcaaatat    1680
aatcttgctt ctaaaattgc ttttaaaaga atccaggaat ccaggaatcc aggaatccag    1740
ccccaggacc agagag                                                    1756
```

<210> SEQ ID NO 3
<211> LENGTH: 34
<212> TYPE: DNA
<213> ORGANISM: Homo sapiens

<400> SEQUENCE: 3

```
gtaccggtgc caccatggcc tgtttgtgga gctt                                  34
```

<210> SEQ ID NO 4
<211> LENGTH: 29
<212> TYPE: DNA
<213> ORGANISM: Homo sapiens

<400> SEQUENCE: 4

```
aggaattccc aggaagacac aaccatcac                                        29
```

<210> SEQ ID NO 5
<211> LENGTH: 300
<212> TYPE: PRT
<213> ORGANISM: Homo sapiens

<400> SEQUENCE: 5

```
Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
            130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
            245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro
            290                 295                 300

<210> SEQ ID NO 6
<211> LENGTH: 186
<212> TYPE: PRT
<213> ORGANISM: Homo sapiens

<400> SEQUENCE: 6

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
50                  55                  60

Pro Gly Arg Ser Pro Leu Pro Ser His Ala Arg Ser Gln Pro Gly Leu
65                  70                  75                  80
```

```
Cys Asn Met Tyr Lys Asp Ser His His Pro Ala Arg Thr Ala His Tyr
                 85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
            115                 120                 125

Ser Gln Gly Lys Gly Ala Glu Gly Gln Arg Pro Gly Phe Gly Tyr Gly
        130                 135                 140

Gly Arg Ala Ser Asp Tyr Lys Ser Ala His Lys Gly Phe Lys Gly Val
145                 150                 155                 160

Asp Ala Gln Gly Thr Leu Ser Lys Ile Phe Lys Leu Gly Gly Arg Asp
                165                 170                 175

Ser Arg Ser Gly Ser Pro Met Ala Arg Arg
                180                 185

<210> SEQ ID NO 7
<211> LENGTH: 277
<212> TYPE: PRT
<213> ORGANISM: Homo sapiens

<400> SEQUENCE: 7

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
        50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
```

-continued

```
                260                 265                 270
Arg Gly Thr Lys Phe
            275
```

<210> SEQ ID NO 8
<211> LENGTH: 242
<212> TYPE: PRT
<213> ORGANISM: Homo sapiens

<400> SEQUENCE: 8

```
Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Phe Val Gly Ile Thr Tyr Ala Leu Thr Val Val Trp
        115                 120                 125

Leu Leu Val Phe Ala Cys Ser Ala Val Pro Val Tyr Ile Tyr Phe Asn
130                 135                 140

Thr Trp Thr Thr Cys Gln Ser Ile Ala Phe Pro Ser Lys Thr Ser Ala
145                 150                 155                 160

Ser Ile Gly Ser Leu Cys Ala Asp Ala Arg Met Tyr Gly Val Leu Pro
                165                 170                 175

Trp Asn Ala Phe Pro Gly Lys Val Cys Gly Ser Asn Leu Leu Ser Ile
            180                 185                 190

Cys Lys Thr Ala Glu Phe Gln Met Thr Phe His Leu Phe Ile Ala Ala
        195                 200                 205

Phe Val Gly Ala Ala Ala Thr Leu Val Ser Leu Leu Thr Phe Met Ile
210                 215                 220

Ala Ala Thr Tyr Asn Phe Ala Val Leu Lys Leu Met Gly Arg Gly Thr
225                 230                 235                 240

Lys Phe
```

<210> SEQ ID NO 9
<211> LENGTH: 247
<212> TYPE: PRT
<213> ORGANISM: Homo sapiens

<400> SEQUENCE: 9

```
Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
50                  55                  60
```

```
Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
            130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
                180                 185                 190

Leu His Arg Thr Phe Asp Pro His Phe Leu Arg Val Pro Cys Trp Lys
                195                 200                 205

Ile Thr Leu Phe Val Ile Val Pro Val Leu Gly Pro Leu Val Ala Leu
                210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 10
<211> LENGTH: 208
<212> TYPE: PRT
<213> ORGANISM: Homo sapiens

<400> SEQUENCE: 10

Met Ala Ser Leu Ser Arg Pro Ser Leu Pro Ser Cys Leu Cys Ser Phe
 1               5                  10                  15

Leu Leu Leu Leu Leu Leu Gln Val Ser Ser Ser Tyr Ala Gly Gln Phe
                 20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
            130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
```

```
                  180                 185                 190

Leu His Arg Thr Phe Gly Gln Phe Leu Glu Glu Leu Arg Asn Pro Phe
            195                 200                 205

<210> SEQ ID NO 11
<211> LENGTH: 224
<212> TYPE: PRT
<213> ORGANISM: Homo sapiens

<400> SEQUENCE: 11

Met Ala Ser Leu Ser Arg Pro Ser Leu Pro Ser Cys Leu Cys Ser Phe
  1               5                  10                  15

Leu Leu Leu Leu Leu Leu Gln Val Ser Ser Tyr Ala Gly Gln Phe
             20                  25                  30

Arg Val Ile Gly Pro Arg His Pro Ile Arg Ala Leu Val Gly Asp Glu
             35                  40                  45

Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
             85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
        130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Glu Ser Phe Gly Val Leu Gly Pro Gln Val Lys
            195                 200                 205

Glu Pro Lys Lys Thr Gly Gln Phe Leu Glu Glu Leu Arg Asn Pro Phe
        210                 215                 220

<210> SEQ ID NO 12
<211> LENGTH: 131
<212> TYPE: PRT
<213> ORGANISM: Homo sapiens

<400> SEQUENCE: 12

Met Ala Ser Leu Ser Arg Pro Ser Leu Pro Ser Cys Leu Cys Ser Phe
  1               5                  10                  15

Leu Leu Leu Leu Leu Leu Gln Val Ser Ser Tyr Ala Asp Pro Phe
             20                  25                  30

Tyr Trp Val Ser Pro Gly Val Leu Val Leu Leu Ala Val Leu Pro Val
             35                  40                  45

Leu Leu Leu Gln Ile Thr Val Gly Leu Ile Phe Leu Cys Leu Gln Tyr
         50                  55                  60

Arg Leu Arg Gly Lys Leu Arg Ala Glu Ile Glu Asn Leu His Arg Thr
 65                  70                  75                  80

Phe Asp Pro His Phe Leu Arg Val Pro Cys Trp Lys Ile Thr Leu Phe
```

```
                85                  90                  95
Val Ile Val Pro Val Leu Gly Pro Leu Val Ala Leu Ile Ile Cys Tyr
            100                 105                 110
Asn Trp Leu His Arg Arg Leu Ala Gly Gln Phe Leu Glu Glu Leu Arg
        115                 120                 125
Asn Pro Phe
    130

<210> SEQ ID NO 13
<211> LENGTH: 131
<212> TYPE: PRT
<213> ORGANISM: Homo sapiens

<400> SEQUENCE: 13

Met Ala Ser Leu Ser Arg Pro Ser Leu Pro Ser Cys Leu Cys Ser Phe
1               5                   10                  15
Leu Leu Leu Leu Leu Gln Val Ser Ser Tyr Ala Asp Pro Phe
            20                  25                  30
Tyr Trp Val Ser Pro Gly Val Leu Val Leu Ala Val Leu Pro Val
        35                  40                  45
Leu Leu Leu Gln Ile Thr Val Gly Leu Ile Phe Leu Cys Leu Gln Tyr
    50                  55                  60
Arg Leu Arg Gly Lys Leu Arg Ala Glu Ile Glu Asn Leu His Arg Thr
65                  70                  75                  80
Phe Asp Pro His Phe Leu Arg Val Pro Cys Trp Lys Ile Thr Leu Phe
                85                  90                  95
Val Ile Val Pro Val Leu Gly Pro Leu Val Ala Leu Ile Ile Cys Tyr
            100                 105                 110
Asn Trp Leu His Arg Arg Leu Ala Gly Gln Phe Leu Glu Glu Leu Arg
        115                 120                 125
Asn Pro Phe
    130

<210> SEQ ID NO 14
<211> LENGTH: 213
<212> TYPE: PRT
<213> ORGANISM: Homo sapiens

<400> SEQUENCE: 14

Met Ala Ser Leu Ser Arg Pro Ser Leu Pro Ser Cys Leu Cys Ser Phe
1               5                   10                  15
Leu Leu Leu Leu Leu Gln Val Ser Ser Ser Tyr Ala Gly Gln Phe
            20                  25                  30
Arg Val Ile Gly Pro Arg His Pro Ile Arg Ala Leu Val Gly Asp Glu
        35                  40                  45
Val Glu Leu Pro Cys Arg Ile Ser Pro Gly Lys Asn Ala Thr Gly Met
    50                  55                  60
Glu Val Gly Trp Tyr Arg Pro Pro Phe Ser Arg Val Val His Leu Tyr
65                  70                  75                  80
Arg Asn Gly Lys Asp Gln Asp Gly Asp Gln Ala Pro Glu Tyr Arg Gly
                85                  90                  95
Arg Thr Glu Leu Leu Lys Asp Ala Ile Gly Glu Gly Lys Val Thr Leu
            100                 105                 110
Arg Ile Arg Asn Val Arg Phe Ser Asp Glu Gly Gly Phe Thr Cys Phe
        115                 120                 125
Phe Arg Asp His Ser Tyr Gln Glu Glu Ala Ala Met Glu Leu Lys Val
```

```
                130                 135                 140
Glu Asp Pro Phe Tyr Trp Val Ser Pro Gly Val Leu Val Leu Leu Ala
145                 150                 155                 160
Val Leu Pro Val Leu Leu Leu Gln Ile Thr Val Gly Leu Ile Phe Leu
                165                 170                 175
Cys Leu Gln Tyr Arg Leu Arg Gly Lys Leu Arg Ala Glu Ile Glu Asn
                180                 185                 190
Leu His Arg Thr Phe Gly Gln Phe Leu Glu Glu Leu Leu Phe His Leu
                195                 200                 205
Glu Ala Leu Ser Gly
            210

<210> SEQ ID NO 15
<211> LENGTH: 229
<212> TYPE: PRT
<213> ORGANISM: Homo sapiens

<400> SEQUENCE: 15

Met Ala Ser Leu Ser Arg Pro Ser Leu Pro Ser Cys Leu Cys Ser Phe
1               5                   10                  15
Leu Leu Leu Leu Leu Leu Gln Val Ser Ser Ser Tyr Ala Gly Gln Phe
                20                  25                  30
Arg Val Ile Gly Pro Arg His Pro Ile Arg Ala Leu Val Gly Asp Glu
                35                  40                  45
Val Glu Leu Pro Cys Arg Ile Ser Pro Gly Lys Asn Ala Thr Gly Met
        50                  55                  60
Glu Val Gly Trp Tyr Arg Pro Pro Phe Ser Arg Val Val His Leu Tyr
65                  70                  75                  80
Arg Asn Gly Lys Asp Gln Asp Gly Asp Gln Ala Pro Glu Tyr Arg Gly
                85                  90                  95
Arg Thr Glu Leu Leu Lys Asp Ala Ile Gly Glu Gly Lys Val Thr Leu
                100                 105                 110
Arg Ile Arg Asn Val Arg Phe Ser Asp Glu Gly Gly Phe Thr Cys Phe
                115                 120                 125
Phe Arg Asp His Ser Tyr Gln Glu Glu Ala Ala Met Glu Leu Lys Val
                130                 135                 140
Glu Asp Pro Phe Tyr Trp Val Ser Pro Gly Val Leu Val Leu Leu Ala
145                 150                 155                 160
Val Leu Pro Val Leu Leu Leu Gln Ile Thr Val Gly Leu Ile Phe Leu
                165                 170                 175
Cys Leu Gln Tyr Arg Leu Arg Gly Lys Leu Arg Ala Glu Ile Glu Asn
                180                 185                 190
Leu His Arg Thr Phe Glu Ser Phe Gly Val Leu Gly Pro Gln Val Lys
                195                 200                 205
Glu Pro Lys Lys Thr Gly Gln Phe Leu Glu Glu Leu Leu Phe His Leu
            210                 215                 220
Glu Ala Leu Ser Gly
225

<210> SEQ ID NO 16
<211> LENGTH: 206
<212> TYPE: PRT
<213> ORGANISM: Homo sapiens

<400> SEQUENCE: 16

Met Ala Ser Leu Ser Arg Pro Ser Leu Pro Ser Cys Leu Cys Ser Phe
```

```
            1               5                  10                 15
Leu Leu Leu Leu Leu Leu Gln Val Ser Ser Tyr Ala Gly Gln Phe
                20                 25                 30

Arg Val Ile Gly Pro Arg His Pro Ile Arg Ala Leu Val Gly Asp Glu
                35                 40                 45

Val Glu Leu Pro Cys Arg Ile Ser Pro Gly Lys Asn Ala Thr Gly Met
 50                 55                 60

Glu Val Gly Trp Tyr Arg Pro Pro Phe Ser Arg Val Val His Leu Tyr
 65                 70                 75                 80

Arg Asn Gly Lys Asp Gln Asp Gly Asp Gln Ala Pro Glu Tyr Arg Gly
                85                 90                 95

Arg Thr Glu Leu Leu Lys Asp Ala Ile Gly Glu Gly Lys Val Thr Leu
                100                105                110

Arg Ile Arg Asn Val Arg Phe Ser Asp Glu Gly Gly Phe Thr Cys Phe
                115                120                125

Phe Arg Asp His Ser Tyr Gln Glu Glu Ala Ala Met Glu Leu Lys Val
                130                135                140

Glu Asp Pro Phe Tyr Trp Val Ser Pro Gly Val Leu Val Leu Leu Ala
145                 150                155                160

Val Leu Pro Val Leu Leu Leu Gln Ile Thr Val Gly Leu Ile Phe Leu
                165                170                175

Cys Leu Gln Tyr Arg Leu Arg Gly Lys Leu Arg Ala Glu Ile Glu Asn
                180                185                190

Leu His Arg Thr Phe Leu Phe His Leu Glu Ala Leu Ser Gly
                195                200                205

<210> SEQ ID NO 17
<211> LENGTH: 203
<212> TYPE: PRT
<213> ORGANISM: Homo sapiens

<400> SEQUENCE: 17

Met Ala Ser Leu Ser Arg Pro Ser Leu Pro Ser Cys Leu Cys Ser Phe
 1               5                  10                 15

Leu Leu Leu Leu Leu Leu Gln Val Ser Ser Ser Tyr Ala Gly Gln Phe
                20                 25                 30

Arg Val Ile Gly Pro Arg His Pro Ile Arg Ala Leu Val Gly Asp Glu
                35                 40                 45

Val Glu Leu Pro Cys Arg Ile Ser Pro Gly Lys Asn Ala Thr Gly Met
 50                 55                 60

Glu Val Gly Trp Tyr Arg Pro Pro Phe Ser Arg Val Val His Leu Tyr
 65                 70                 75                 80

Arg Asn Gly Lys Asp Gln Asp Gly Asp Gln Ala Pro Glu Tyr Arg Gly
                85                 90                 95

Arg Thr Glu Leu Leu Lys Asp Ala Ile Gly Glu Gly Lys Val Thr Leu
                100                105                110

Arg Ile Arg Asn Val Arg Phe Ser Asp Glu Gly Gly Phe Thr Cys Phe
                115                120                125

Phe Arg Asp His Ser Tyr Gln Glu Glu Ala Ala Met Glu Leu Lys Val
                130                135                140

Glu Asp Pro Phe Tyr Trp Val Ser Pro Gly Val Leu Val Leu Leu Ala
145                 150                155                160

Val Leu Pro Val Leu Leu Leu Gln Ile Thr Val Gly Leu Ile Phe Leu
                165                170                175
```

```
Cys Leu Gln Tyr Arg Leu Arg Gly Lys Leu Arg Ala Glu Ile Glu Asn
            180                 185                 190

Leu His Arg Thr Phe Gly Lys Phe Arg His Val
            195                 200

<210> SEQ ID NO 18
<211> LENGTH: 171
<212> TYPE: PRT
<213> ORGANISM: Homo sapiens

<400> SEQUENCE: 18

Met Ala Ser Leu Ser Arg Pro Ser Leu Pro Ser Cys Leu Cys Ser Phe
1               5                   10                  15

Leu Leu Leu Leu Leu Gln Val Ser Ser Tyr Ala Gly Gln Phe
            20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
    130                 135                 140

Glu Val Ser His Ser Val Thr Gln Asp Trp Leu Gln Trp His Asp His
145                 150                 155                 160

Gly Ser Leu Gln Pro Pro Pro Arg Leu Lys
                165                 170

<210> SEQ ID NO 19
<211> LENGTH: 51
<212> TYPE: DNA
<213> ORGANISM: Homo sapiens

<400> SEQUENCE: 19
tggcatttct gcattcgaag aagaatctga gagaaacctg acgcagggag c              51

<210> SEQ ID NO 20
<211> LENGTH: 197
<212> TYPE: PRT
<213> ORGANISM: Homo sapiens

<400> SEQUENCE: 20

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80
```

```
Cys Asn Met Tyr Lys Asp Ser His His Pro Ala Arg Thr Ala His Tyr
                 85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 21
<211> LENGTH: 15
<212> TYPE: PRT
<213> ORGANISM: Homo sapiens

<400> SEQUENCE: 21

Glu Asn Pro Val Val His Phe Phe Lys Asn Ile Val Thr Pro Arg
1               5                   10                  15

<210> SEQ ID NO 22
<211> LENGTH: 15
<212> TYPE: PRT
<213> ORGANISM: Homo sapiens

<400> SEQUENCE: 22

Ala Arg Thr Ala His Tyr Gly Ser Leu Pro Gln Lys Ser His Gly
1               5                   10                  15

<210> SEQ ID NO 23
<211> LENGTH: 19
<212> TYPE: PRT
<213> ORGANISM: Homo sapiens

<400> SEQUENCE: 23

Asp Glu Asn Pro Val Val His Phe Phe Lys Asn Ile Val Thr Pro Arg
1               5                   10                  15
Thr Pro Pro

<210> SEQ ID NO 24
<211> LENGTH: 19
<212> TYPE: PRT
<213> ORGANISM: Homo sapiens

<400> SEQUENCE: 24

Leu Ser Arg Phe Ser Trp Gly Ala Glu Gly Gln Arg Pro Gly Phe Gly
1               5                   10                  15
Tyr Gly Gly

<210> SEQ ID NO 25
<211> LENGTH: 14
<212> TYPE: PRT
<213> ORGANISM: Homo sapiens
```

```
<400> SEQUENCE: 25

His Lys Gly Phe Lys Gly Val Asp Ala Gln Gly Thr Leu Ser
1               5                   10

<210> SEQ ID NO 26
<211> LENGTH: 40
<212> TYPE: PRT
<213> ORGANISM: Homo sapiens

<400> SEQUENCE: 26

Cys Gly Cys Gly His Glu Ala Leu Thr Gly Thr Glu Lys Leu Ile Glu
1               5                   10                  15

Thr Tyr Phe Ser Lys Asn Tyr Gln Asp Tyr Glu Tyr Leu Ile Asn Val
            20                  25                  30

Ile His Ala Phe Gln Tyr Val Ile
        35                  40

<210> SEQ ID NO 27
<211> LENGTH: 21
<212> TYPE: PRT
<213> ORGANISM: Homo sapiens

<400> SEQUENCE: 27

Gly Thr Glu Lys Leu Ile Glu Thr Tyr Phe Ser Lys Asn Tyr Gln Asp
1               5                   10                  15

Tyr Glu Tyr Leu Ile
            20

<210> SEQ ID NO 28
<211> LENGTH: 30
<212> TYPE: PRT
<213> ORGANISM: Homo sapiens

<400> SEQUENCE: 28

Tyr Thr Thr Gly Ala Val Arg Gln Ile Phe Gly Asp Tyr Lys Thr Thr
1               5                   10                  15

Ile Cys Gly Lys Gly Leu Ser Ala Thr Val Thr Gly Gly Gln
            20                  25                  30

<210> SEQ ID NO 29
<211> LENGTH: 51
<212> TYPE: PRT
<213> ORGANISM: Homo sapiens

<400> SEQUENCE: 29

Asn Thr Trp Thr Thr Cys Gln Ser Ile Ala Phe Pro Ser Lys Thr Ser
1               5                   10                  15

Ala Ser Ile Gly Ser Leu Cys Ala Asp Ala Arg Met Tyr Gly Val Leu
            20                  25                  30

Pro Trp Asn Ala Phe Pro Gly Lys Val Cys Gly Ser Asn Leu Leu Ser
        35                  40                  45

Ile Cys Lys
        50

<210> SEQ ID NO 30
<211> LENGTH: 9
<212> TYPE: PRT
<213> ORGANISM: Homo sapiens

<400> SEQUENCE: 30

Phe Phe Arg Asp His Ser Tyr Gln Glu
```

-continued

<210> SEQ ID NO 31
<211> LENGTH: 9
<212> TYPE: PRT
<213> ORGANISM: Homo sapiens

<400> SEQUENCE: 31

Leu Val Gly Asp Glu Val Glu Leu Pro
1               5

<210> SEQ ID NO 32
<211> LENGTH: 9
<212> TYPE: PRT
<213> ORGANISM: Homo sapiens

<400> SEQUENCE: 32

Leu Arg Ile Arg Asn Val Arg Phe Ser
1               5

<210> SEQ ID NO 33
<211> LENGTH: 9
<212> TYPE: PRT
<213> ORGANISM: Homo sapiens

<400> SEQUENCE: 33

Tyr Trp Val Ser Pro Gly Val Leu Val
1               5

<210> SEQ ID NO 34
<211> LENGTH: 9
<212> TYPE: PRT
<213> ORGANISM: Homo sapiens

<400> SEQUENCE: 34

Tyr Arg Pro Pro Phe Ser Arg Val Val
1               5

<210> SEQ ID NO 35
<211> LENGTH: 197
<212> TYPE: PRT
<213> ORGANISM: Homo sapiens

<400> SEQUENCE: 35

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
                20                  25                  30

Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
        50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His

```
                130                 135                 140
Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Val Ser Ser Glu Glu
        195

<210> SEQ ID NO 36
<211> LENGTH: 197
<212> TYPE: PRT
<213> ORGANISM: Homo sapiens

<400> SEQUENCE: 36

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
        50                  55                  60

Pro Gly Arg Ser Pro Leu Pro Ser His Ala Arg Ser Gln Pro Gly Leu
65                  70                  75                  80

Cys Asn Met Tyr Lys Asp Ser His Pro Ala Arg Thr Ala His Tyr
                85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
            115                 120                 125

Ser Gln Gly Lys Gly Arg Gly Leu Ser Leu Ser Arg Phe Ser Trp Gly
130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 37
<211> LENGTH: 171
<212> TYPE: PRT
<213> ORGANISM: Homo sapiens

<400> SEQUENCE: 37

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Asp Ser His His Pro
```

```
                50                  55                  60
Ala Arg Thr Ala His Tyr Gly Ser Leu Pro Gln Lys Ser His Gly Arg
 65                  70                  75                  80

Thr Gln Asp Glu Asn Pro Val Val His Phe Phe Lys Asn Ile Val Thr
                 85                  90                  95

Pro Arg Thr Pro Pro Ser Gln Gly Lys Gly Arg Gly Leu Ser Leu
                100                 105                 110

Ser Arg Phe Ser Trp Gly Ala Glu Gly Gln Arg Pro Gly Phe Gly Tyr
            115                 120                 125

Gly Gly Arg Ala Ser Asp Tyr Lys Ser Ala His Lys Gly Phe Lys Gly
            130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170
```

<210> SEQ ID NO 38
<211> LENGTH: 160
<212> TYPE: PRT
<213> ORGANISM: Homo sapiens

<400> SEQUENCE: 38

```
Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
 65                  70                  75                  80

Thr Gln Asp Glu Asn Pro Val Val His Phe Phe Lys Asn Ile Val Thr
                 85                  90                  95

Pro Arg Thr Pro Pro Ser Gln Gly Lys Gly Ala Glu Gly Gln Arg
                100                 105                 110

Pro Gly Phe Gly Tyr Gly Gly Arg Ala Ser Asp Tyr Lys Ser Ala His
            115                 120                 125

Lys Gly Phe Lys Gly Val Asp Ala Gln Gly Thr Leu Ser Lys Ile Phe
            130                 135                 140

Lys Leu Gly Gly Arg Asp Ser Arg Ser Gly Ser Pro Met Ala Arg Arg
145                 150                 155                 160
```

<210> SEQ ID NO 39
<211> LENGTH: 74
<212> TYPE: PRT
<213> ORGANISM: Homo sapiens

<400> SEQUENCE: 39

```
Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Ser Leu Pro Gln
                20                  25                  30

Lys Ser His Gly Arg Thr Gln Asp Glu Asn Pro Val Val His Phe Phe
            35                  40                  45
```

```
Lys Asn Ile Val Thr Pro Arg Thr Pro Pro Ser Gln Gly Lys Gly
    50                  55                  60

Arg Gly Leu Ser Leu Ser Arg Phe Ser Trp
65                  70
```